United States Patent
Disilvestro

(10) Patent No.: US 7,347,874 B2
(45) Date of Patent: Mar. 25, 2008

(54) IN VIVO JOINT IMPLANT CYCLE COUNTER

(75) Inventor: Mark R. Disilvestro, Ft. Wayne, IN (US)

(73) Assignee: Depuy Products, Inc., Warsaw, IN (US)

( * ) Notice: Subject to any disclaimer, the term of this patent is extended or adjusted under 35 U.S.C. 154(b) by 0 days.

(21) Appl. No.: 10/887,766

(22) Filed: Jul. 9, 2004

(65) Prior Publication Data

US 2005/0010299 A1   Jan. 13, 2005

Related U.S. Application Data

(60) Provisional application No. 60/486,762, filed on Jul. 11, 2003.

(51) Int. Cl.
*A61F 2/30* (2006.01)

(52) U.S. Cl. ............ 623/18.12; 623/914; 600/587

(58) Field of Classification Search ......... 623/16.11, 623/18.11, 18.12, 914, 23.16; 600/587, 595; 73/172
See application file for complete search history.

(56) References Cited

U.S. PATENT DOCUMENTS

| | | | |
|---|---|---|---|
| 4,045,825 A | 9/1977 | Stroot | |
| 4,576,148 A * | 3/1986 | Koerner et al. | 601/40 |
| 4,675,670 A | 6/1987 | Lalonde et al. | |
| 5,197,488 A * | 3/1993 | Kovacevic | 600/595 |
| 5,376,128 A | 12/1994 | Bozeman | |
| 5,395,033 A | 3/1995 | Byrne et al. | |
| 5,458,655 A | 10/1995 | Bozeman | |
| 5,465,619 A | 11/1995 | Sotack et al. | |
| 5,480,454 A | 1/1996 | Bozeman | |
| 5,769,875 A | 6/1998 | Peckham et al. | |
| 5,776,171 A | 7/1998 | Peckham et al. | |
| 5,831,430 A | 11/1998 | Pfanstiehl et al. | |
| 5,954,758 A | 9/1999 | Peckham et al. | |
| 6,026,328 A | 2/2000 | Peckham et al. | |
| 6,163,725 A | 12/2000 | Peckham et al. | |
| 6,228,900 B1 | 5/2001 | Shen et al. | |
| 6,245,109 B1 | 6/2001 | Mendes et al. | |
| 6,281,264 B1 | 8/2001 | Salovey et al. | |
| 6,281,679 B1 | 8/2001 | King et al. | |
| 6,332,089 B1 | 12/2001 | Acker et al. | |

(Continued)

FOREIGN PATENT DOCUMENTS

WO   WO 00/65981   11/2000

OTHER PUBLICATIONS

Graichen, F., et al; Four-Channel Telemetry System for In Vivo Measurement of Hip Joint Forces (1991). J. Biomed. Eng. 1991, vol. 13, Sep.

(Continued)

*Primary Examiner*—Brian E. Pellegrino

(57) ABSTRACT

A joint endoprosthesis system has two prosthetic components to be affixed to two bones of a human joint. A sensor and electronic components are affixed to one of the prosthetic components so that a record can be maintained of the number of times the patient moves the prosthetic joint in a particular way, such as in walking. This information is stored within the electronic components and selectively transmitted to an external system for interpretation of the data. The caregiver can use this data to counsel the patient on life-style changes or to prescribe therapeutic treatments if available.

11 Claims, 19 Drawing Sheets

U.S. PATENT DOCUMENTS

| | | | |
|---|---|---|---|
| 6,400,989 B1 | 6/2002 | Eckmiller | |
| 6,447,448 B1 | 9/2002 | Ishikawa et al. | |
| 6,454,781 B1 | 9/2002 | Witt et al. | |
| 6,473,652 B1 | 10/2002 | Sarwa et al. | |
| 6,498,944 B1 | 12/2002 | Ben-Haim et al. | |
| 6,507,189 B2 | 1/2003 | Woolsey et al. | |
| 6,558,229 B2 | 5/2003 | Kimura et al. | |
| 6,563,308 B2 | 5/2003 | Nagano et al. | |
| 6,573,706 B2 | 6/2003 | Mendes et al. | |
| 6,583,630 B2 | 6/2003 | Mendes et al. | |
| 6,610,096 B2* | 8/2003 | MacDonald | 623/23.16 |
| 6,679,920 B2 | 1/2004 | Biedermann et al. | |
| 6,821,299 B2* | 11/2004 | Kirking et al. | 623/20.14 |
| 2001/0000187 A1 | 4/2001 | Peckham et al. | |
| 2002/0133175 A1 | 9/2002 | Carson | |
| 2002/0147455 A1 | 10/2002 | Carson | |
| 2004/0019382 A1* | 1/2004 | Amirouche et al. | 623/18.11 |
| 2004/0034355 A1 | 2/2004 | Govari et al. | |

OTHER PUBLICATIONS

Graichen, F., et al; Inductively Powered Telemetry System for In Vivo Measurement With Orthopaedic Implants (1995); Biotelemetry XIII, Mar. 26-31, 1995—Williamsburg, VA.

Miller, Joel S., et al; Molecule-Based Magnets—An Overview (2000). MRS Bulletin, Nov.

Seedhom, B.B., et al; A Technique for the Study of Geometry and Contact in Normal and Artificial Knee Joints (1972). Wear—Elsevier Sequoia S.A., Lausanne—Printed in the Netherlands.

Troyk, Philip R., et al; Design and Implementation of an Implantable Goniometer (1986); IEEE Transactions on Biomedical Engineering, vol. BME-33, No. 2, Feb.

Bhadra, N., MD, et al; Implementation of an implantable joint-angle transducer, Journal of Rehabilitation Research and Development, May/Jun. 2002, pp. 411-422, vol. 39, No. 3.

Bragdon, C.R., et al; Experimental assessment of precision and accuracy of radiostereometric analysis for the determination of polyethylene wear in a total hip replacement model. Journal of Orthopaedic Research, 2002, pp. 688-695, 20.

Cicuttini, F. M., et al; Tibial and femoral cartilage changes in knee osteoarthritis. Ann Rheum Dis Oct. 2001; pp. 977-980, 60.

Conrozier, T., et al; Quantitative radiography in osteoarthritis: Computerized measurement of radiographic knee and hip joint space. Bailliere's Clinical Rheumatology, Aug. 1996, pp. 429-433, vol. 10, No. 3.

Hilliquin, P., et al; Quantitative assessment of joint space width with an electronic caliper; Osteoarthritis and Cartilage Jul. 2002; pp. 542-546, 10.

Hyldahl, H.C.,MD, et al; Does Metal Backing Improve Fixation of Tibial Component in Unicondylar Knee Arthroplasty? A Randomized Radiostereometric Analysis. The Journal of Arthroplasty, 2001, pp. 174-179, vol. 16 No. 2.

Ilchmann, T., Thesis Radiographic assessment of cup migration and wear after hip replacement. Acta Orthopaedica Scandinavica, Oct. 1997, vol. 68, No. 276.

Johnson, M.W., et al; Implantable Transducer for Two-Degree of Freedom Joint Angle Sensing, IEEE Transactions on Rehabilitation Engineering, Sep. 1999, pp. 349-359, vol. 7, No. 3.

Karrholm, J., MD, et al; Radiostereometry of Hip Prostheses Review of Methodology and Clinical Results, Clinical Orthopaedics and Related Research, 1997, pp. 94-110 No. 344.

Lanyon, P., et al; Radiographic assessment of symptomatic knee osteoarthritis in the community: definitions and normal joint space. Ann Rheum Dis 1998, pp. 595-601 No. 57.

Onsten I, et al; Wear in uncemented porous and cemented polyethylene sockets: A Randomised, Radiosterometric Study. The Journal of Bone and Joint Surgery Br, Mar. 1998; pp. 345-350, 80(2).

Pavelka, K., et al; Correlation between knee roentgenogram changes and clinical symptoms in osteoarthritis. Rev. Rhum. Mal. Osteoartic., 1992, pp. 553-559, 59 (9).

Ryd, L., et al; Methods for determining the accuracy of radiostereometric analysis (RSA), Acta Orthopaedic Scandinavica, 2000, pp. 403-408, 71 (4).

Selvik, G., Roentgen stereophotogrammetry A method for the study of the kinematics of the skeletal system. Acta Orthopaedica Scandinavica, 1989, vol. 60, No. 232, Munksgaard Copenhagen.

Sychterz, Christi J., MS, et al; Effect of Radiographic Quality on Computer-Assisted Head Penetration Measurements. Clinical Orthopaedics and Related Research, 2001, pp. 150-158, No. 386.

Vrooman, H.A., et al; Fast and accurate automated measurements in digitized stereophotogrammetric radiographs. Journal of Biomechanics, 1998, pp. 491-498, 31.

International search report dated Nov. 25, 2005, for corresponding international application PCT/US2004/22254.

* cited by examiner

IN VIVO JOINT IMPLANT CYCLE COUNTER

CROSS-REFERENCE TO RELATED APPLICATIONS

This application claims priority to U.S. Provisional Application Ser. No. 60/486,762 filed on Jul. 11, 2003 by Mark R. DiSilvestro, entitled "In Vivo Joint Implant Cycle Counter," which is incorporated by reference herein in its entirety.

FIELD OF THE INVENTION

The present invention relates to joint endoprostheses systems.

BACKGROUND OF THE INVENTION

Human joints can become damaged as a result of accident or illness. Such damage can be, for example, to the articular cartilage covering the ends of the bones at the joint as well as the intra-articular cartilage between the ends of the adjacent bones of the joint. When the damage to the joint is severe, a joint endoprosthesis can be implanted to improve the comfort and mobility of the patient.

Joint endoprostheses have been developed to replace native tissue of several human joints. There are a variety of knee prostheses, hip prostheses, shoulder prostheses, ankle prostheses and wrist prostheses available to relieve patient suffering. Such devices are available, for example, from the assignee of the present invention, DePuy Orthopaedics, Inc. of Warsaw, Ind.

Standard joint endoprostheses include metal components that are affixed to the articulating ends of the bones of the joint and commonly include a bearing component positioned between the metal components. Standard bearing components of joint endoprostheses have a surface against which one of the metal components articulates. For example, hip endoprostheses include a metal femoral component to be affixed to the proximal femur and a metal cup to be affixed to the acetabulum. Many of these standard hip endoprostheses include a liner in the acetabular cup against which the femoral component articulates. Knee prostheses commonly include a femoral component to be affixed to the distal femur and a tibial component to be affixed to the proximal tibia. Bearings are typically between the femoral and tibial components. Similar systems with bearings are available to replace other joints in the body.

Standard bearings for joint endoprostheses are made of ultrahigh molecular weight polyethylene (UHMWPE), ceramic and metal. Bearing wear is problematic in the orthopaedic field. Several patents have addressed the problem particles produced by UHMWPE wear, and the association of these particles with osteolysis. See, for example: U.S. Pat. No. 6,281,264, "Chemically crosslinked ultrahigh molecular weight polyethylene for artificial human joints" and U.S. Pat. No. 6,228,900 "Crosslinking of polyethylene for low wear using radiation and thermal treatments."

Undue bearing wear can result in conditions requiring that the joint endoprosthesis be removed and replaced in a revision procedure. Accordingly, early detection of bearing wear could find use as a signal to the orthopaedic surgeon that some type of intervention is needed before the condition degenerates to the point of requiring revision surgery. For example, the surgeon may determine that the patient needs to make some lifestyle changes if revision is to be postponed. Moreover, if therapeutic agents to treat early stage osteolysis are available, these agents could be administered before the condition degenerates to the point where revision surgery is necessary.

SUMMARY OF THE INVENTION

The present invention addresses the need to provide readily accessible data for monitoring joint endoprostheses after implantation. Data on the extent of use of the joint endoprosthesis is made available to allow the caregiver to intervene if necessary if the joint endoprosthesis is being used excessively.

In one aspect, the present invention provides a joint endoprosthesis system to be implanted in a patient. The system comprises a first prosthetic component to be affixed to one bone of the joint, a second prosthetic component to be affixed to the other bone of the joint, a sensor and a counter. The sensor is for generating a signal each time the bones of the joint are in a predetermined condition. The counter is for storing the number of signals generated by the sensor.

In another aspect, the present invention provides a joint endoprosthesis system comprising a first prosthetic component to be affixed to one bone of the joint, a second prosthetic component to be affixed to the other bone of the joint, a sensor, a counter and a transmitter. The sensor serves to generate a signal each time the bones are in a predetermined position. The counter is for storing the incremental number of signals generated by the sensor. The transmitter is for selectively transmitting a signal having a characteristic related to the incremental count recorded by the counter. The system also includes a first power source for supplying continuous power to the counter and a second power source for selectively supplying power to the transmitter.

In another aspect, the present invention provides a method of monitoring use of an implanted joint endoprosthesis system. The joint endoprosthesis system includes a first prosthetic component affixed to one bone of the joint and a second prosthetic component affixed to another bone of the joint. The first and second prosthetic components are movable through a plurality of positions. The method comprises the steps of generating a signal each time the first and second prosthetic components are in a predetermined position, storing an incremental count of the number of signals generated within the patient's body, and converting the incremental count stored into a transmittable signal. The transmittable signal is transmitted to a position outside of the patient's body and the incremental count is determined outside of the patient's body.

BRIEF DESCRIPTION OF THE DRAWINGS

The invention will be better understood by reference to the figures of the drawings wherein like numbers denote like parts throughout and wherein.

DETAILED DESCRIPTION OF THE ILLUSTRATED EMBODIMENTS

Figure 19:
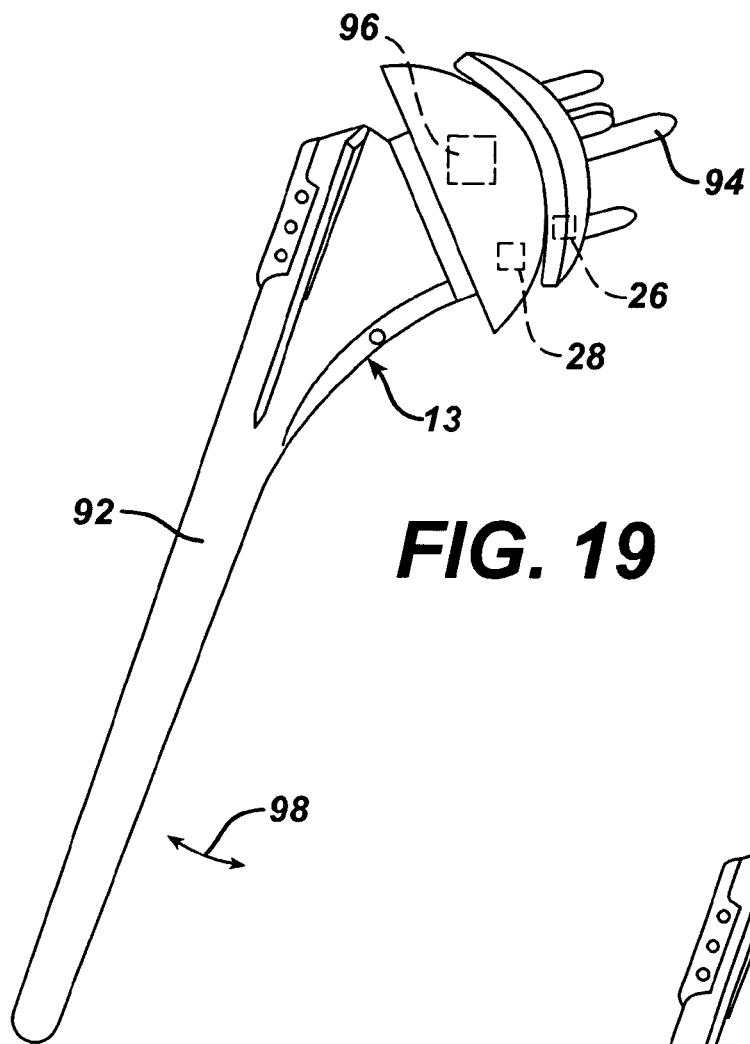
FIG. 19 is a side elevation of a shoulder joint endoprosthesis system, showing the humeral and glenoid components in one position.
Figure 20:
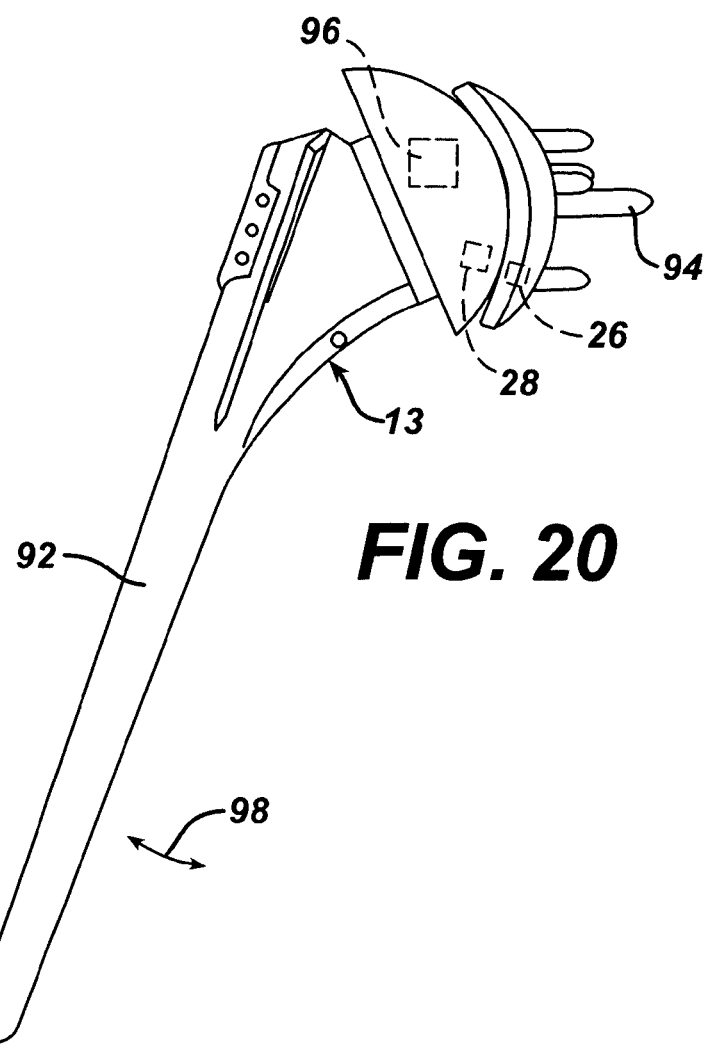
FIG. 20 is a side elevation of the shoulder joint endoprosthesis system of FIG. 21, showing the humeral and glenoid components in a second position.
Figure 21:
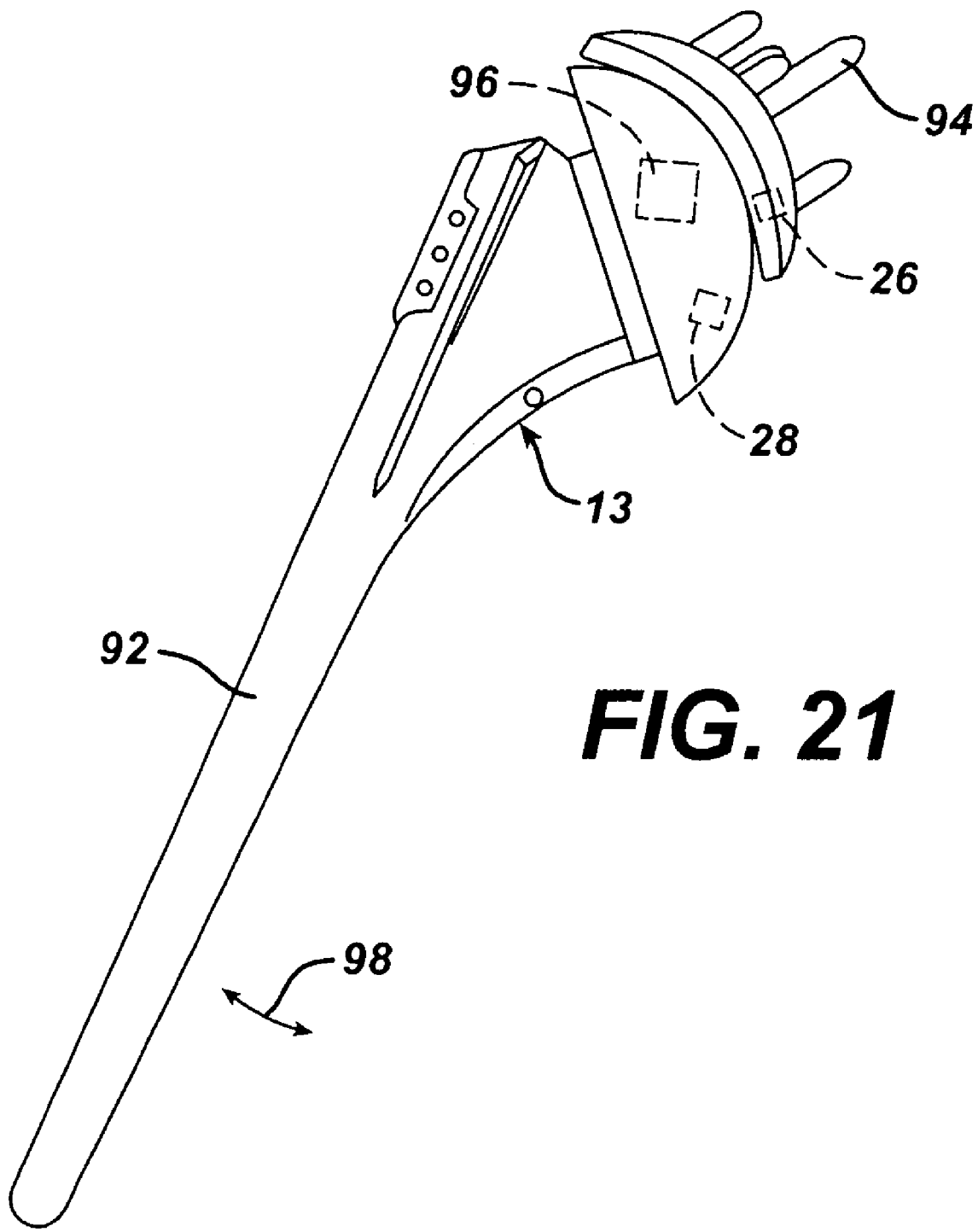
FIG. 21 is a side elevation of the shoulder joint endoprosthesis system of FIGS. 21–22, showing the humeral and glenoid components in a third position.
Figure 22:
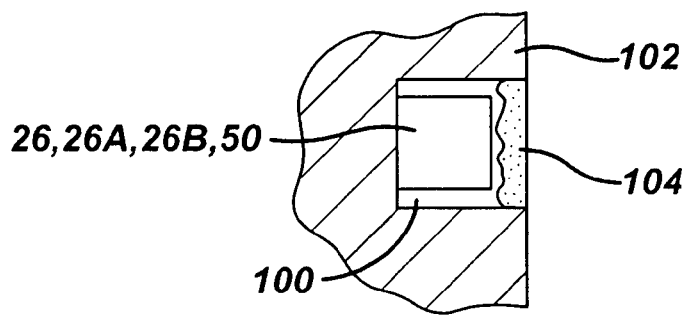
FIG. 22 is a is a partial cross-section of a body of an endoprosthesis component with a signal source secured within a recess or cavity in the body portion of the endoprosthesis component.
Figure 23:
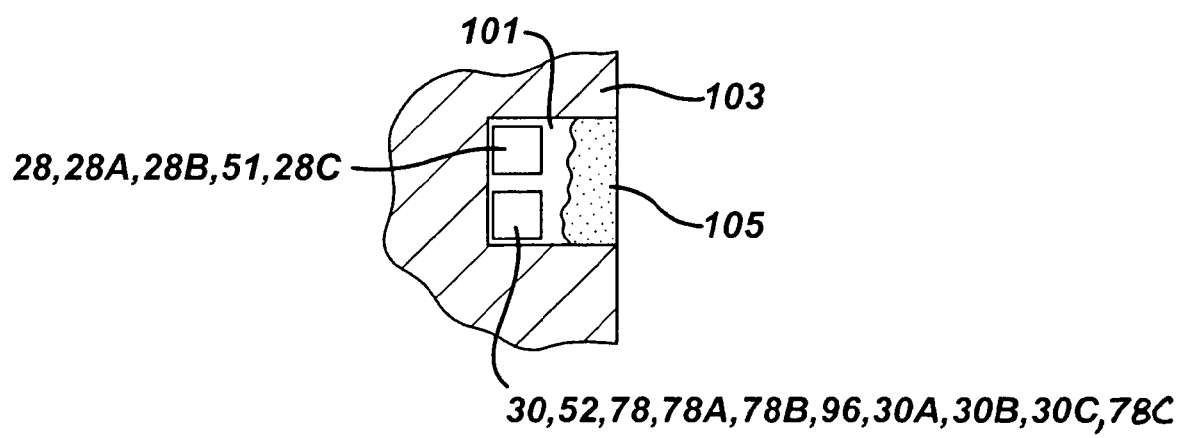
FIG. 23 is another partial cross-section of a portion of a body of an endoprosthesis component with a sensor and associated electronics secured within a recess or cavity in the body portion of the endoprosthesis component.
Figure 24:
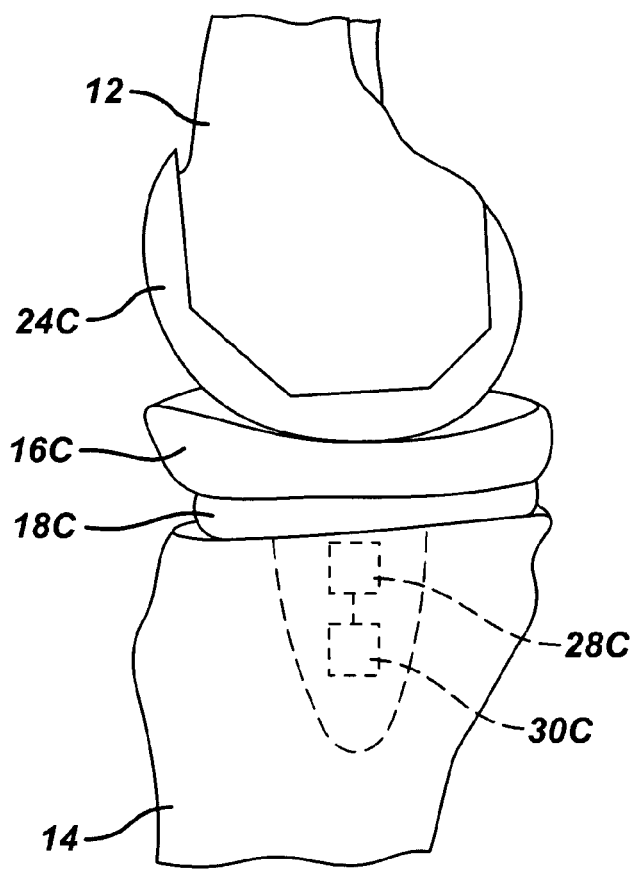
FIG. 24 is a side elevation of a knee joint endoprosthesis system implanted on a distal femur and proximal tibia, showing the bones and prosthetic components in extension as when the patient is in a standing position.
Figure 25:
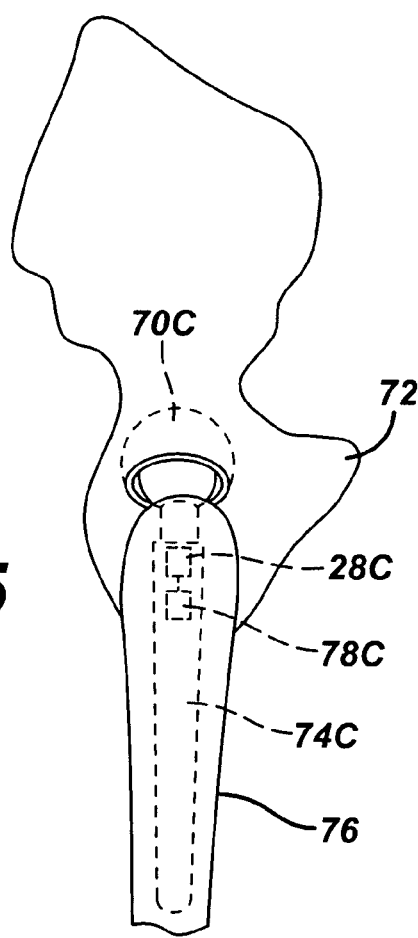
FIG. 25 is a side elevation of a hip joint endoprosthesis system implanted on a portion of the hip bone and the proximal femur, showing the bones and prosthetic components in extension as when the patient is in a normal standing position.

Joint endoprosthesis systems incorporating the principles of the present invention are illustrated in the accompanying drawings. In FIGS. 1–11 and 24, the system is a knee endoprosthesis system. In FIGS. 12–18 and 25, the system is a hip endoprosthesis system. In FIGS. 19–21, the system is a shoulder endoprosthesis system. FIGS. 22–23 are applicable to all of the illustrated endoprosthesis systems. It should be understood that FIGS. 1–25 are diagrammatic illustrations of these systems, and do not depict all of the features of the prosthetic components. It should also be understood that the teachings of the present invention can also be applied to other joint endoprostheses, including wrist, elbow and ankle endoprostheses and endoprostheses for use with the digits of the extremities.

Each of the illustrated knee endoprosthesis and hip endoprosthesis systems includes three basic components: a first prosthetic component to be affixed to one bone of the joint, a second prosthetic component to be affixed to the other bone of the joint, and a bearing component to be positioned at the joint articulation, in the joint space between the first and second prosthetic components. In the knee endoprosthesis system, the first component comprises a distal femoral component with condyles defining an articulating surface. The second component comprises a proximal tibial component. The bearing is a tibial bearing carried by the tibial component. The tibial bearing has an upper surface bearing against the condyles of the distal femoral component. The interface of the condyles of the distal femoral component and the upper surface of the tibial bearing defines the articulation of the knee prosthesis system. The tibial bearing occupies the joint space between the distal femoral and proximal tibial components, and the thickness of the tibial bearing corresponds with the thickness of the joint space in the knee endoprosthesis system. In the hip prosthesis system, the first component comprises an acetabular cup or shell to be affixed to a prepared space in the patient's hip bone. The second component comprises a proximal femoral component. The proximal femoral component has a femoral head defining an articulating surface. The bearing is an acetabular liner carried by the acetabular cup. The acetabular liner has a curved surface bearing against the femoral head of the proximal femoral component. The interface of the femoral head and the curved surface of the acetabular liner defines the articulation of the hip prosthesis system. The acetabular liner occupies the joint space between the acetabular cup and the femoral head, and the thickness of the acetabular liner corresponds with the thickness of the joint space of the hip endoprosthesis system. Analogous components are present in other joint endoprosthesis systems.

The illustrated shoulder endoprosthesis system includes two basic components. The first component comprises a humeral component, including a stem and a humeral head. The second component comprises a glenoid component. The surface of the humeral head defines an articulating surface. The glenoid component has a surface that bears against the humeral head. The interface of the humeral head and the glenoid component defines the articulation of the shoulder joint prosthesis system. A portion of the glenoid component occupies the joint space, and the thickness of this portion of the glenoid component corresponds with the thickness of the joint space of the shoulder endoprosthesis system.

In each of the illustrated endoprosthesis systems, the implants are designed to articulate as the patient goes through normal life routines, such as walking, sitting and lifting. During such normal routines, the distal surface of the femoral condyles of the knee endoprosthesis articulate against the tibial bearing surface, the surface of the femoral head of the hip endoprosthesis articulates against the acetabular liner and the surface of the humeral head of the shoulder endoprosthesis articulates against the glenoid component.

The femoral, tibial and bearing components for the knee endoprosthesis system of the present invention can have features of known commercially available knee endoprosthesis systems, such as those available from DePuy Orthopaedics, Inc. of Warsaw, Ind. Similarly, the femoral, acetabular and bearing components for the hip endoprosthesis system of the present invention can have features of known commercially available hip systems, such as those available from DePuy Orthopaedics, Inc. of Warsaw, Ind. The humeral and glenoid components of the shoulder endoprosthesis system of the present invention can also have features of known commercially available shoulder systems, such as those available from DePuy Orthopaedics, Inc. of Warsaw, Ind. The components of these systems can also have features of the commercially available products of other suppliers of knee, hip and shoulder endoprostheses, such as those available from Zimmer, Inc. of Warsaw, Ind., Biomet, Inc. of Warsaw, Ind., Stryker Howmedica Osteonics, Inc. of Mahwah, N.J., and Smith & Nephew, Inc. of Memphis, Tenn. It should be understood that it is anticipated that the endoprosthesis systems of the present invention may include subsequent improvements to these commercial products. It should also be understood that although standard materials such as cobalt chrome, titanium, polyethylene and ceramic, can be used for these components of the joint endoprostheses, the present invention is not limited to any particular material for any of the components unless expressly set forth in the claims.

In addition to the standard components, the endoprosthesis systems of the present invention include additional components for monitoring use of the joint endoprosthesis systems after implantation. As explained in more detail below, these additional components include a signal source, a recording device and associated electronics that provide data for determining the number of times the joint endoprosthesis is cycled through a particular motion or motions. These additional components may be permanently affixed to the standard joint endoprosthesis components, and the standard joint endoprosthesis components may be modified slightly to allow for this permanent affixation.

As used herein, "signal" is intended to encompass fields, such as magnetic and electrical fields, flux densities, currents and waves such as acoustic and radio-frequency waves, for example. "Signal source" is intended to encompass devices such as permanent magnets, load sensors and electronic circuits that produce such signals. Accordingly, "signal" and "signal source" should not be limited to a particular type of signal or signal source unless expressly called for in the claims.

In the illustrated embodiments, the signal source serves to generate a first signal. If the signal source is a permanent magnet, the signal generated is a magnetic field or a magnetic flux density. If the signal source is a radio-frequency (RF) transmitter, the signal generated comprises radio-frequency waves. Other types of electronic signal sources could serve to generate eddy currents or an electric field. If the signal source is a load sensor or strain gauge, the signal generated comprises an electric current or voltage.

"Proximity sensor" is intended to encompass devices such as switches, transducers, transponders, and electromagnetic sensors. The sensor functions to sense a characteristic of the first signal generated by the signal source. For example, the sensor may function to sense the magnitude or orientation of the magnetic field or flux density generated by a permanent magnet at a particular location, or may function to sense the frequency, amplitude or phase of a radio-frequency (RF) wave generated by an RF transmitter. The sensor may also serve to generate a second signal that has a characteristic that varies depending on some characteristic of the signal it has sensed. In embodiments relying upon signals such as eddy currents or electric fields, the signal source and sensor can be part of a single common element.

"Target" is intended to include a component in which eddy currents or electrical charges are induced. In the case of a joint endoprosthesis system, the target can comprise a surface or portion of a surface of one of the metal components, such as the proximal surface of the proximal tibial component or the distal surface of the condyles of the distal femoral component.

Generally, in the illustrated embodiments, where a signal source is used, the signal source is positioned on one side of the articulation or joint space of the joint endoprosthesis and the sensor or target is positioned on the opposite side of the endoprosthesis articulation. The signal source is at a fixed position with respect to one of the endoprosthesis components and the sensor or target is at a fixed position with respect to the other endoprosthesis component on the opposite side of the articulation. Since the positions of the signal source and sensor or target are fixed with respect to the bone-affixed components of the joint endoprosthesis, changes in the relative positions of the signal source and sensor or target that correspond with particular movements of the patient can be counted. Thus, if the distance between the signal source and sensor or target decreases to a predetermined level, this decrease in distance corresponds with a particular relative position of the bone-affixed components of the endoprosthesis system. In other words, the proximity of the signal source and sensor or target corresponds with a particular relative position of the bone-affixed components. By counting the number of times the bone-affixed components are in a particular relative position, use of the endoprosthesis system can be monitored. Thus, with the endoprosthesis system of the present invention, the amount of walking, running, lifting or changes in positions can be monitored. If the caregiver (such as the orthopaedic surgeon)

determines that the patient's use of the implant exceeds the normal range of use for such an implant, the caregiver can intervene before the patient exhibits a condition requiring revision surgery. For example, the caregiver could suggest lifestyle changes that would lessen overuse of the endoprosthesis.

The system may also compensate for movement of the implant components through migration or subsidence for example. Such compensation can be accomplished by selecting a sensor with a threshold activation range that is unaffected by a range of movement associated with migration or subsidence. It should also be understood that non-weight-bearing movement of the implant components (such as when the patient stretches the affected limb) will be counted as part of the cycle count process, and that consideration may be given to such movements in analyzing the results of the cycle counting.

Figure 1:
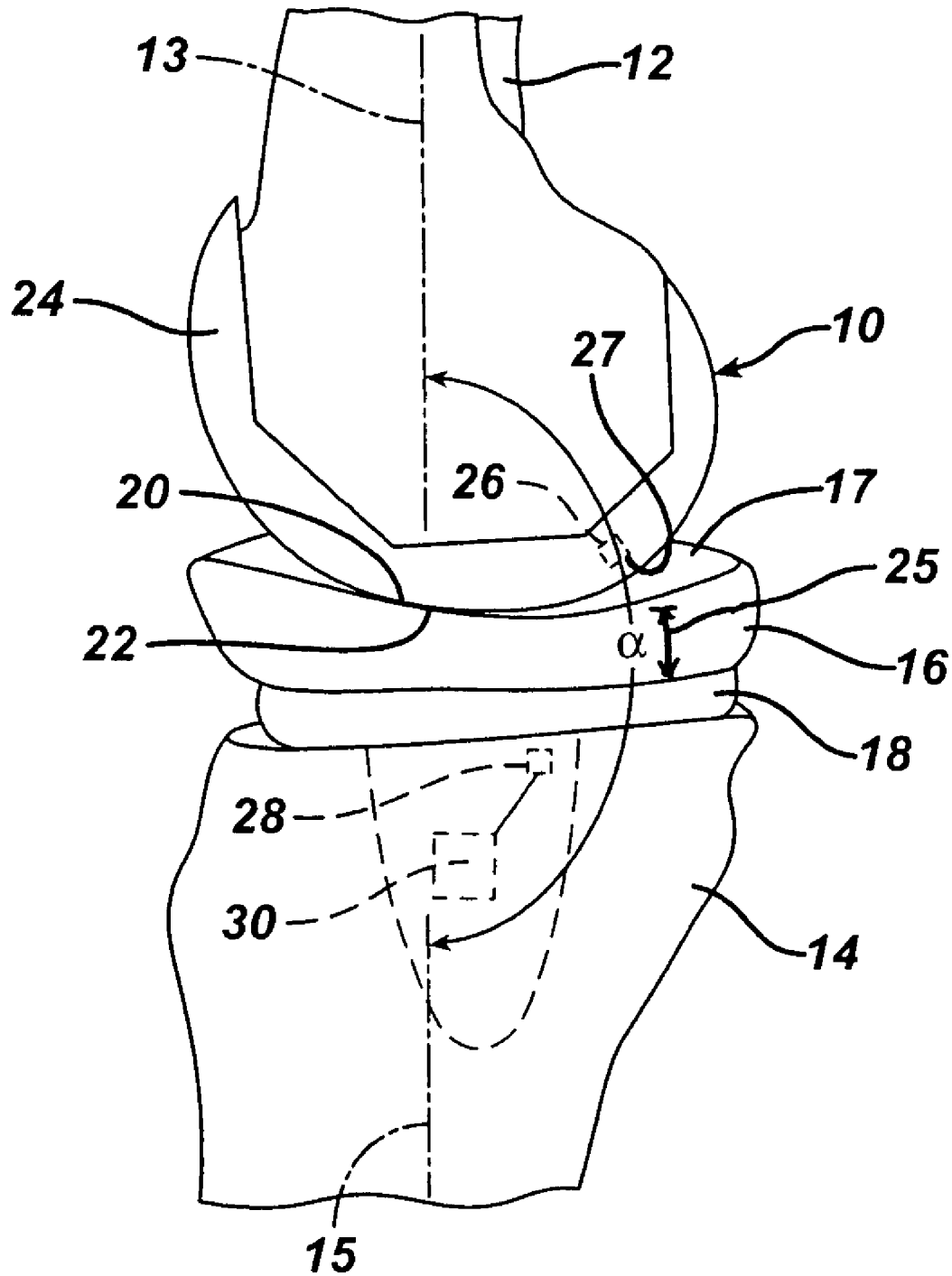
FIG. 1 is a side elevation of a first embodiment of a knee joint endoprosthesis system implanted on a distal femur and proximal tibia, showing the bones and prosthetic components in extension as when the patient is in a standing position.
Figure 2:
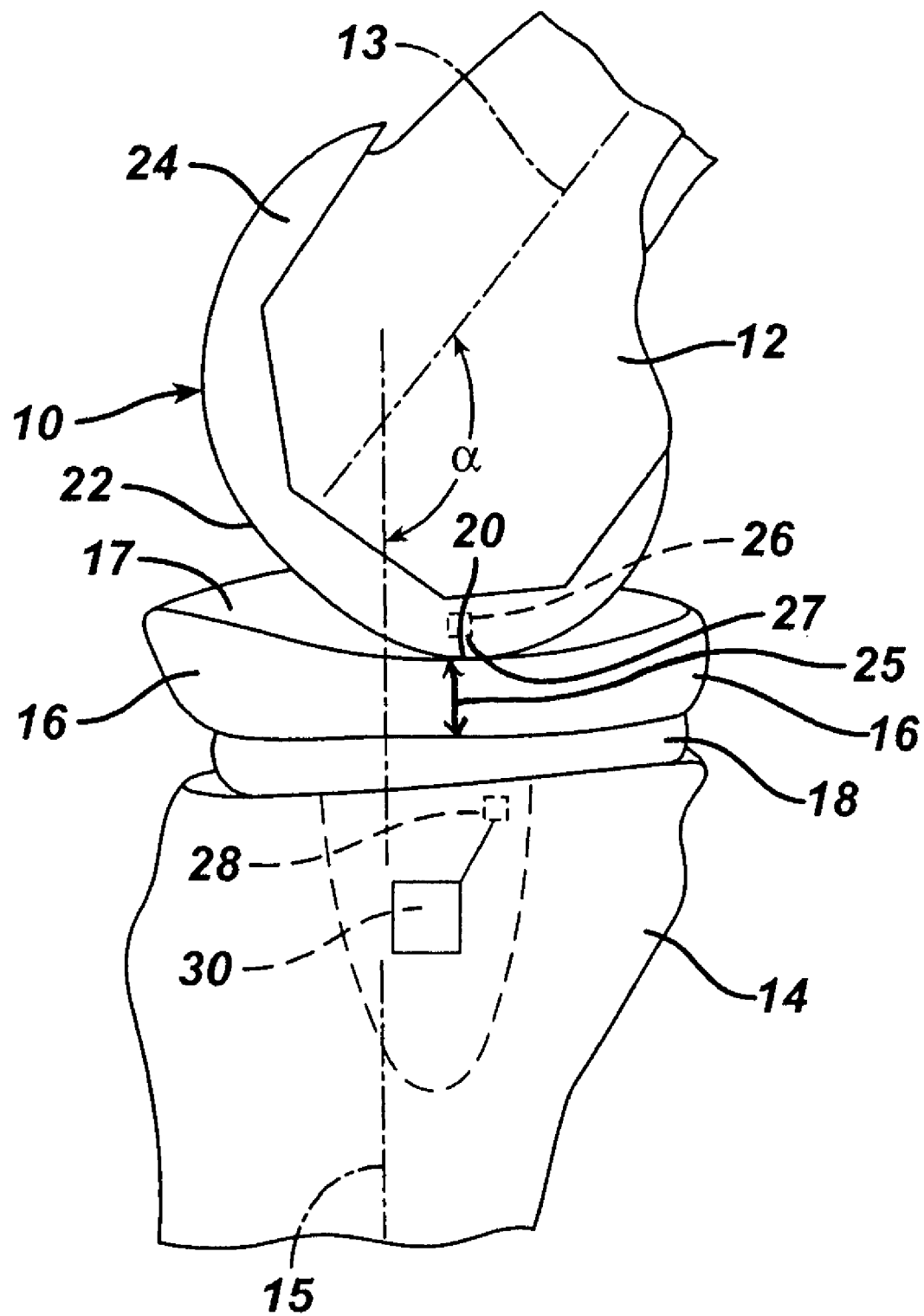
FIG. 2 is a side elevation of the knee joint endoprosthesis system of FIG. 1, showing the bones and prosthetic components when the leg is slightly flexed, as when the patient is walking.
Figure 3:
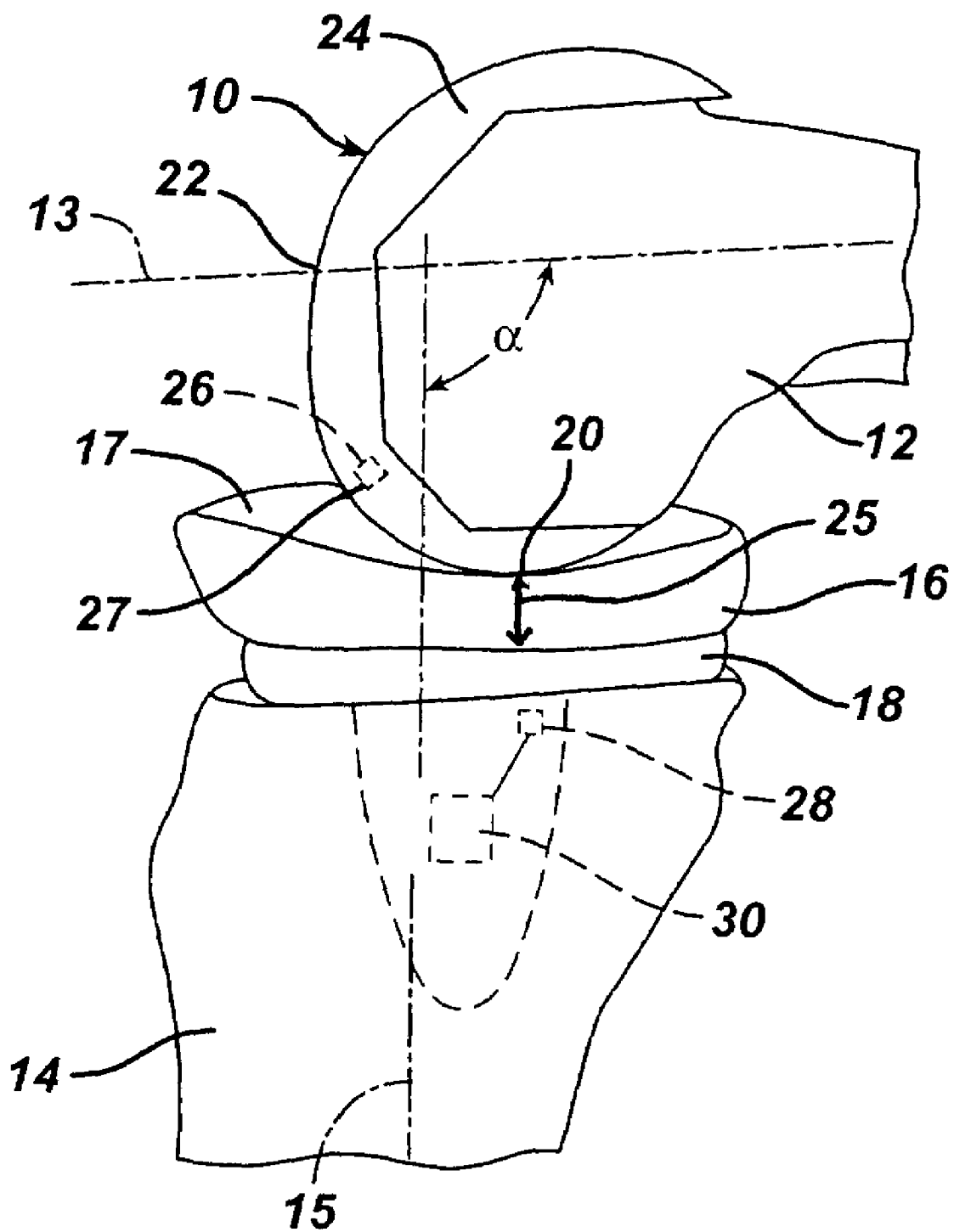
FIG. 3 is a side elevation of the knee joint endoprosthesis system of FIGS. 1–2, showing the bones and prosthetic components when the leg is fully flexed as when the patient is squatting.

Referring now to FIGS. 1–3, a knee endoprosthesis system 10 incorporating the principles of the present invention is illustrated implanted on the distal end of the femur 12 and proximal end of the tibia 14. The illustrated system 10 includes a tibial bearing 16 that is carried by the proximal tibial component 18. The proximal tibial component 18 is affixed to the proximal end of the tibia 14. The tibial bearing 16 has a contoured proximal surface 17, against which the condyles 22 of the distal femoral component 24 bear. The distal femoral component 24 is affixed to the distal end of the femur 12. Articulation of the joint is at the interface of the proximal surface 17 of the tibial bearing 16 and the condyles 22 of the distal femoral component 24. The joint articulation is indicated at 20 in FIGS. 1–3; the joint space occupied by the tibial bearing 16 is indicated at 25 in FIGS. 1–3.

In the embodiment of FIGS. 1–3, a signal source 26 is permanently affixed to the distal femoral prosthetic component 24 at a predetermined position. A sensor 28 is permanently affixed to the proximal tibial prosthetic component 18 at a predetermined position. Associated electronics 30 are also permanently affixed to the proximal tibial prosthetic component 18, as described in more detail below.

The signal source 26 in the first illustrated embodiment comprises a permanent magnet. A suitable neodymium magnet is available from Ogallala Electronics Division, Ogallala, Nebr. of the Arnold Engineering group of SPS Technologies, Inc. of Jenkintown, Pa., for example. However, it should be understood that the present invention is not limited to use of any particular type of magnet unless expressly called for in the claims; other magnetic field generators, such as coils as described in "Medical Sensor Having Power Coil, Sensor Coil and Control Chip", U.S. patent application Ser. No. 10/198,514 filed Jul. 18, 2002 by Govari et al. (the disclosure of which is incorporated by reference herein in its entirety) could be used. In addition, the present invention is not limited to the use of a magnet or other magnetic field generator as the signal source, unless expressly called for in the claims.

The sensor 28 in the first illustrated embodiment comprises a Hall effect switch. A Hall effect switch produces an electrical signal in response to the magnetic field strength or flux density generated by the permanent magnet. A suitable Hall effect switch is commercially available from Allegro Microsystems of Hillsborough, N.C. and is identified as a Micropower Ultrasensitive Omnipolar Hall Effect switch, part A3212ELHLT5. It should be understood that this switch is identified as an example only; the present invention is not limited to use of any particular Hall effect switch. In addition, other magnetic field sensitive elements, such as a Hall effect transducer, magnetoresistive element or a magnetic transistor, are anticipated to be useful as the sensor 28 of the present invention. Moreover, the present invention is not limited to use of a switch or transducer as the sensor. The sensor could comprise other elements, such as an RF receiver, for example, as described in more detail below.

As can be seen from a comparison of FIGS. 1–3, the alignment of the signal source 26 and the sensor 28 and the orientation of the signal source 26 in the first illustrated embodiment varies with the relative positions of the patient's femur and tibia. These relative positions of the patient's femur and tibia vary with the patient's activity.

FIG. 1 illustrates the knee when the patient is in a standing position. In this position, the mechanical axis 13 of the femur 12 and the mechanical axis 15 of the tibia define an angle $\alpha$ in the sagittal plane. This angle is about 180° when the patient is standing, and the signal source 26 and the sensor 28 are offset from each other in this plane, the sensor 28 being more anterior than the signal source 26. Moreover, the pole 27 of the permanent magnet forming the signal source 26 is oriented away from the sensor 28 when the patient is standing. Because of this offset and orientation, the magnetic field strength or flux density at the sensor 28 will be at a known level below the maximum magnetic field strength or flux density. The threshold of the Hall effect switch can be selected so that the sensor 28 does not generate any electrical signal when the patient is standing as in FIG. 1.

FIG. 2 illustrates the knee when the patient has bent the knee slightly, as in the case where the patient is walking. In this position, the angle $\alpha$ between the axes 13, 15 decreases and the signal source 26 and sensor 28 are vertically aligned. Moreover, the pole 27 of the permanent magnet forming the signal source 26 is directed toward the Hall effect switch forming the sensor 28. Thus, the positions and orientations of the signal source 26 and sensor 28 are such that the magnetic field strength or flux density is at its maximum when the patient's leg is bent slightly as in FIG. 2. The threshold of the Hall effect switch forming the sensor 28 is such that the Hall effect switch generates an electrical signal when the patient's knee is in the position shown in FIG. 2, but not when the patient's knee is in the position shown in either FIG. 1 or 3. Thus, when the angle $\alpha$ is at a predetermined level, the Hall effect switch (sensor 28) generates an electrical signal. The angle $\alpha$ for a system monitoring walking may be between 75° and 150°, for example.

FIG. 3 illustrates the knee when the knee has been fully flexed. At this angle between the femur and tibia, the pole 27 of the permanent magnet forming the signal source 26 is directed away from the Hall effect switch forming the sensor 28. In addition, the signal source 26 and sensor 28 are offset from each other in the sagittal plane: the sensor 28 is in a more posterior position than the signal source 26. Because of this offset and orientation, the magnetic field strength or flux density at the sensor 28 will be at a known level below the maximum magnetic field strength or flux density. The threshold of the Hall effect switch can be selected so that the sensor 28 does not generate any electrical signal when the patient's leg is in the position shown in FIG. 3.

Thus, in the first illustrated embodiment, a signal is produced when the patient is walking. This signal is produced each time the patient moves his or her knee through the position shown in FIG. 2; in other words, a signal is produced with each stride taken by the patient. It should be understood that the present invention is not limited to sensing the knee joint position shown in FIG. 2. Alternatively or additionally, for example, the signal source and sensor could be positioned and oriented so that a signal is produced each time the patient's knee is in the position shown in FIG. 3.

To produce usable data from these signals, each electrical signal generated by the Hall effect switch (sensor 28) is transmitted to the electronic components 30 of the knee endoprosthesis system 10. As illustrated in FIGS. 1–3, these electronic components 30 may be permanently affixed to a portion of the proximal tibial prosthetic component 18 and may be electrically connected to the sensor 28.

Figure 4:
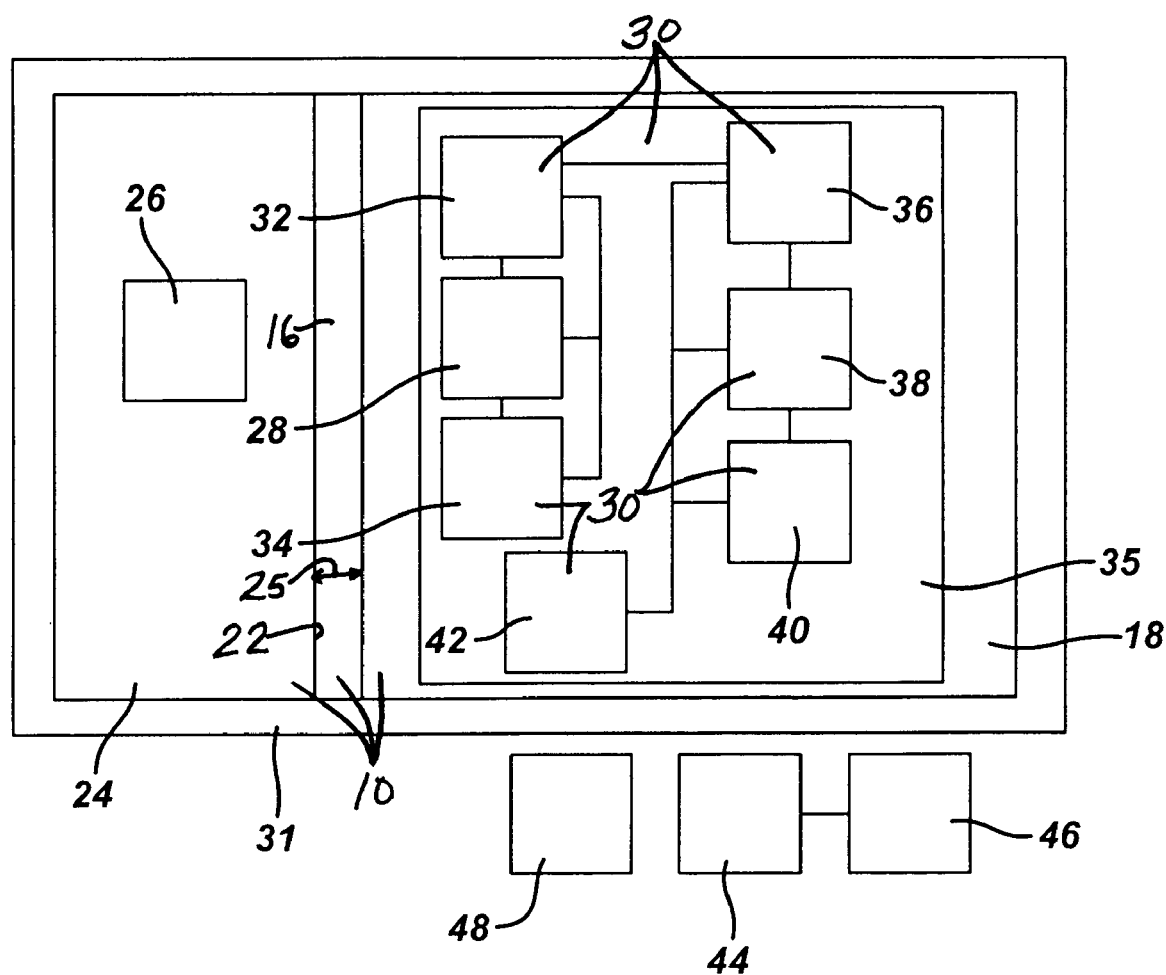
FIG. 4 is a schematic illustration of the components of the knee joint endoprosthesis system of FIGS. 1–4, showing external components as well as those implanted in the patient.

As shown schematically in FIG. 4, the electronic components 30 of the first illustrated knee endoprosthesis system include the following components: a counter component 32, a first internal power source 34, a printed circuit board 35, a modulator 36, a transmitter 38, an internal antenna 40 and a second internal power source 42.

A suitable 24-bit counter component 32 is commercially available from Texas Instruments, Inc., Dallas, Tex., part no. ADS1210P. The counter component should be able to keep a running count of the number of signals it receives from the Hall effect switch (sensor 28). In other words, each time the Hall effect switch is turned on, the change in voltage output of the switch will result in an incremental increase by the counter, which will thereby store the "equivalent" cycles of use of the joint.

Figure 5:
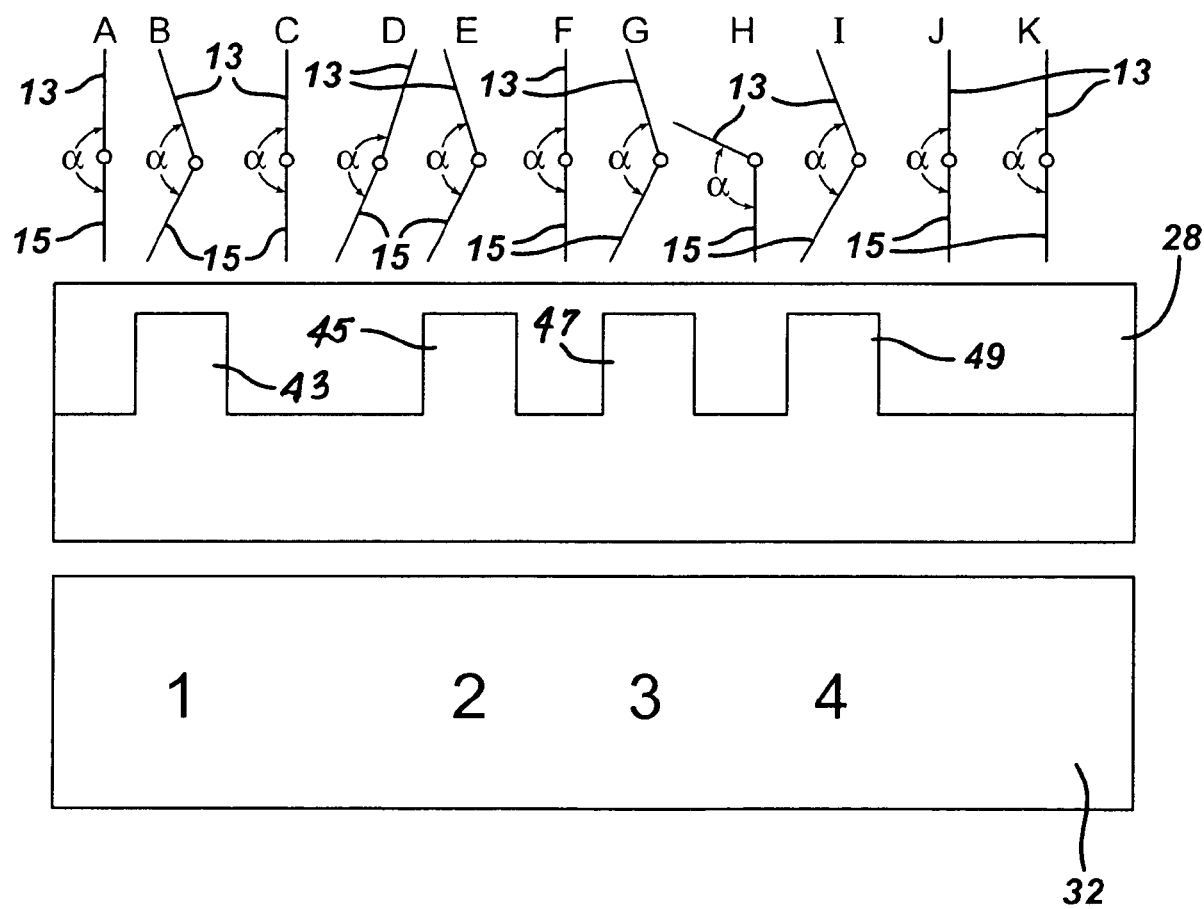
FIG. 5 is a schematic illustration of operation of the knee joint endoprosthesis system of FIGS. 1–4, illustrating the relationship between various positions of the patient's leg, the output of a sensor and an incremental count that is maintained by the endoprosthesis system.

FIG. 5 illustrates the operation of the sensor 28 and counter 32 schematically with reference to changes in the relationship between the axes 13, 15 of the patient's leg as the patient stands, walks and sits. In this example, the permanent magnet (signal source 26) and Hall effect switch (sensor 28) are positioned and oriented so that the Hall effect switch generates a voltage signal to coincide with each stride taken by the patient when walking but to not generate a signal when the patient is standing still or sitting. To accomplish this result, the permanent magnet and switch may be oriented to generate a signal each time the angle α is in a range such as 70°–135°, for example. Thus, when the patient is standing as illustrated schematically at positions A, C, F, J and K in FIG. 5, there is no voltage signal from the Hall effect switch (sensor 28) and the counter 32 does not register any incremental change. Similarly, when the patient is sitting as in position H of FIG. 5, the Hall effect switch (sensor 28) does not generate a signal and the counter 32 does not register any incremental change. However, when the patient moves his or her leg through positions B, E, G and I of FIG. 5, the angle α falls within the predetermined range, a voltage output is created by the Hall effect switch 28, shown at 43, 45, 47 and 49 in FIG. 5, each time the leg is in this position, and the counter 32 registers the rise in voltage as a single increment as shown by the numbers "1", "2", "3" and "4" in FIG. 5.

The first internal power source 34 comprises a battery in the illustrated embodiment, such as a lithium iodine cell available from Wilson Greatbatch Technologies, Inc. of Clarence, N.Y. The battery is connected to both the Hall effect switch (sensor 28) and the counter 32 so that each of these components has a continuous supply of power to continuously monitor use of the implant. Alternatively, the first internal power source 34 could be a ferrite coil that is inductively coupled to a primary coil worn by the patient in an optimal location, such as near the joint.

The counter 32 is electrically connected or coupled to the printed circuit board 35. The counter 32 is also electrically connected or coupled to the modulator 36 which is mounted on the printed circuit board 35 in the illustrated embodiment. The modulator 36 serves to convert the incremental count number created and stored in the counter 32 to an encoded signal that can be transmitted from the internal transmitter 38 to a location outside of the patient's body. For example, the modulator 36 can encode a particular count onto an RF wave by means of varying signal amplitude, frequency or phase. The modulator 36 is electrically connected or coupled to the transmitter 38 so that this RF wave can be transmitted outside of the patient's body through the internal antenna 40. The transmitter 38 can also be mounted on the printed circuit board 35. It should be understood that the present invention is not limited to the use of RF waves unless expressly called for in the claims; other signals that can be encoded and transmitted from within the patient's body to outside the patient's body could be used.

Suitable printed circuit boards 35 are commercially available from Advanced Circuits of Aurora, Colo. The particular lay out and design of the circuit board will depend on factors such as the types of parts used for the signal source and sensor. Generally, the circuit board may be designed or laid out to minimize its size and eliminate capacitive coupling. It should be understood that the invention is not limited to any particular printed circuit board unless expressly called for in the claims.

Suitable modulators 36 are commercially available from Texas Instruments, Inc., Dallas, Tex., in the form of electronic chips. Alternatively, the modulator 36 and transmitter 38 could be part of a single component.

In the illustrated embodiment, the transmitter 38 comprises a radio-frequency transmitter. Suitable internal transmitters 38 are commercially available from Texas Instruments Inc. in the form of electronic chips. The desired characteristics of the transmitter 38 may vary depending on other components of the system; in general, the transmitter will be of an appropriate size for implantation, will transmit at a desired frequency and will not consume excessive power. Although the modulator 36 and transmitter 38 are illustrated as separate elements, a single element could perform both of these functions. Moreover, it should be understood that the present invention is not limited to any particular type of transmitter or transmission signal unless expressly called for in the claims.

Other possible types of transmitters and types of signals include optical data transmission. An IBM personal area network may also be usable as a transmitter. Acoustic energy transmission, capacitive telemetry (using electric fields) and inductive telemetry (using magnetic fields) are also possible alternatives for transmission in the present invention.

The transmitter 38 is electrically connected or coupled to the internal antenna 40 and is permanently affixed to the one of the bone-affixed prosthetic components such as prosthetic tibial component 18, as in the embodiment of FIGS. 1–4. In the illustrated embodiment, the antenna 40 is hermetically sealed. A suitable antenna 40 is available from Microstrain of Williston, Vt. The antenna can be mounted on the printed circuit board 35 if desired.

The illustrated embodiment also includes a second internal power source 42. The second internal power source 42 can comprise a battery, or an inductive power source such as ferrite coil. A suitable ferrite coil is a small wound coil available commercially from MicroStrain, Inc. of Williston, Vt. The necessary characteristics of such a wound coil will depend to some extent on the design and selection of the other electronic components; power, frequency and size of the coil can be adjusted to suit the other components of the system. Alternatively, a suitable ferrite coil could be wound using standard equipment such as that available from Aumann North America, Inc. of Fort Wayne, Ind. The power component 42 is electrically connected to supply power to the printed circuit board 35, modulator 36, transmitter 38 and antenna 40. It should be understood that it may not be necessary to include a second power source; all of the implanted electrical components associated with one side of the joint articulation could be connected to be powered by a single power source, such as an internal battery. However, since the Hall effect switch (sensor 28) and counter 32 of the first illustrated embodiment receive a continuous power supply, it may be desirable to maximize the useful life of the power source used for these elements by utilizing a second power source for the components that are only used periodically. The second power source can be electrically connected or coupled to the printed circuit board, and can also be mounted on the printed circuit board. Alternatively, instead of providing a second power source, the power for the secondary system 36, 38, 40 could come from the first power source 34 using an inductively activated switch.

As shown schematically in FIG. 4, an external receiver 44 and data interpretation device 46 can be provided at the point of care, such as in a physician's office or at a hospital. The external receiver 44 can comprise a radio-frequency antenna that is connected to receive the signal from the internal antenna 40 and to provide a second signal to the data interpretation device 46. The data interpretation device 46 can be a standard computer programmed to demodulate the radio-frequency signal received from the internal transmitter 38 and internal antenna 40. The data interpretation device 46 can also be a hand-held personal computer, a personal desk assistant, a laptop computer or any custom-designed data acquisition device. The data interpretation device 46 can be programmed to perform calculations necessary to convert the received and demodulated signal into the number of cycles recorded by the counter 32. It is anticipated that a software engineer or programmer could readily program the external data interpretation device 46 to perform this calculation. This number of cycles can be compared to a base reference to determine if the patient's life-style is likely to adversely affect the useful life of any one of the joint endoprosthesis components.

If the second internal power source 42 comprises an inductor, an external power source 48 can also be provided at the point of care. The external power source 48 can comprise an external coil that generates a strong localized electromagnetic or magnetostatic field that is coupled to the implanted ferrite coil (second internal power source 42) to thereby supply power to the implanted electronics 36, 38, 40. Suitable external coils are commercially available from Microstrain Inc. of Williston, Vt. Generally, since the external coils are likely to be used in close proximity to the patient, it may be desirable to select or design an external coil that will not irritate or excessively heat the patient's skin and that can be easily handled by the operator or medical technician. The external coil should be able to supply a sufficient field at the design frequency to stimulate the internal power coil. A suitable ferrite coil could also be wound using standard equipment such as that available from Aumann North America, Inc. of Fort Wayne, Ind.

Figure 6:
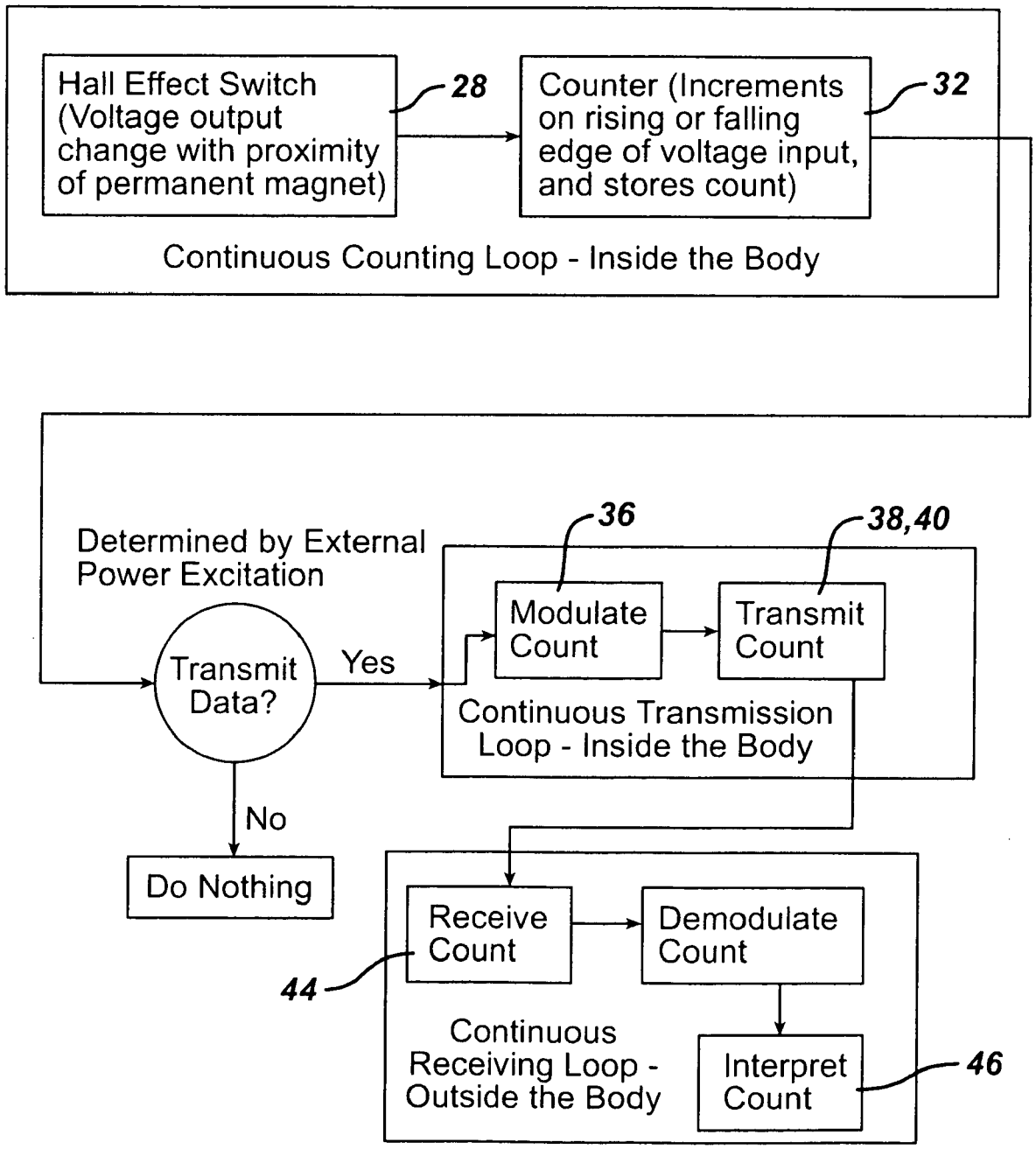
FIG. 6 is a flow chart illustrating use of the knee endoprosthesis system of FIGS. 1–5.

FIG. 6 illustrates a possible flow diagram for information for the first illustrated embodiment of the present invention. As there shown, the Hall effect switch 28 and counter 32 are in a continuous loop inside the body so that the counter 32 is continuously storing information (the incremental count in this embodiment). If there is no external power source, the other implanted electronics 36, 38, 40 remain inactive. When an external power source is applied, the second implanted power source supplies electrical power to the modulator 36 and transmitter 38. The modulator 36 converts the count received from the counter 32 into a transmittable signal and the transmitter 38 transmits this transmittable signal in the form of a modulated radio-frequency wave through the internal antenna 40. The external antenna 44 receives the transmitted wave that has been encoded by the board or chip 36 and this encoded wave is interpreted in the external computer 46 to provide the count in the form of a numerical value for use by the caregiver.

If a proximity sensor relying upon magnetic field or flux is to be used, the components 26, 28 can be positioned to minimize the effects of other magnetic fields to prevent undesired activation of the sensor. In addition, steps may be taken to prevent or limit demagnetization of the permanent magnet.

Figure 7:
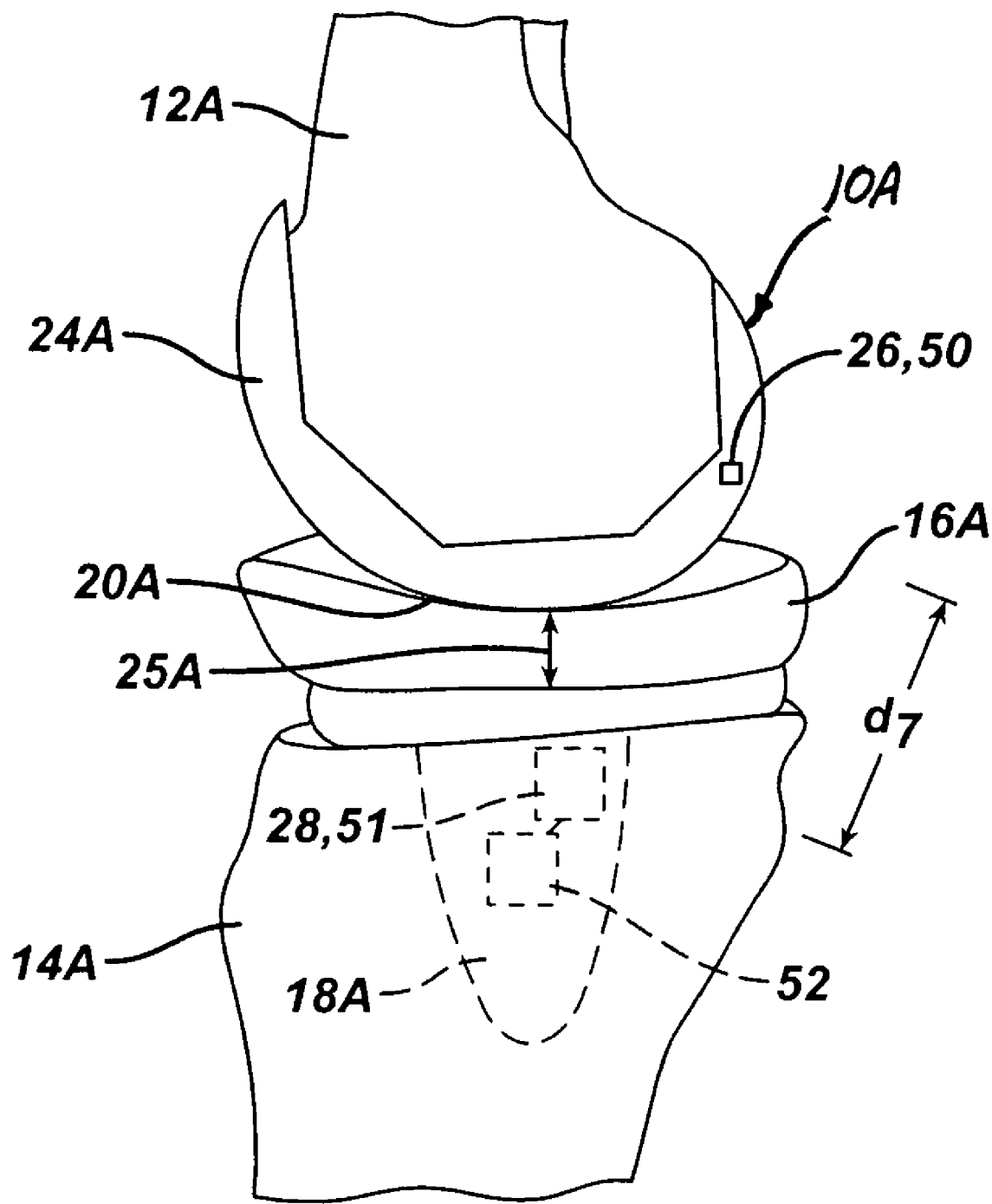
FIG. 7 is a side elevation of a second embodiment of a knee joint endoprosthesis system implanted on a distal femur and proximal tibia, showing the bones and prosthetic components in extension as when the patient is in a standing position.
Figure 8:
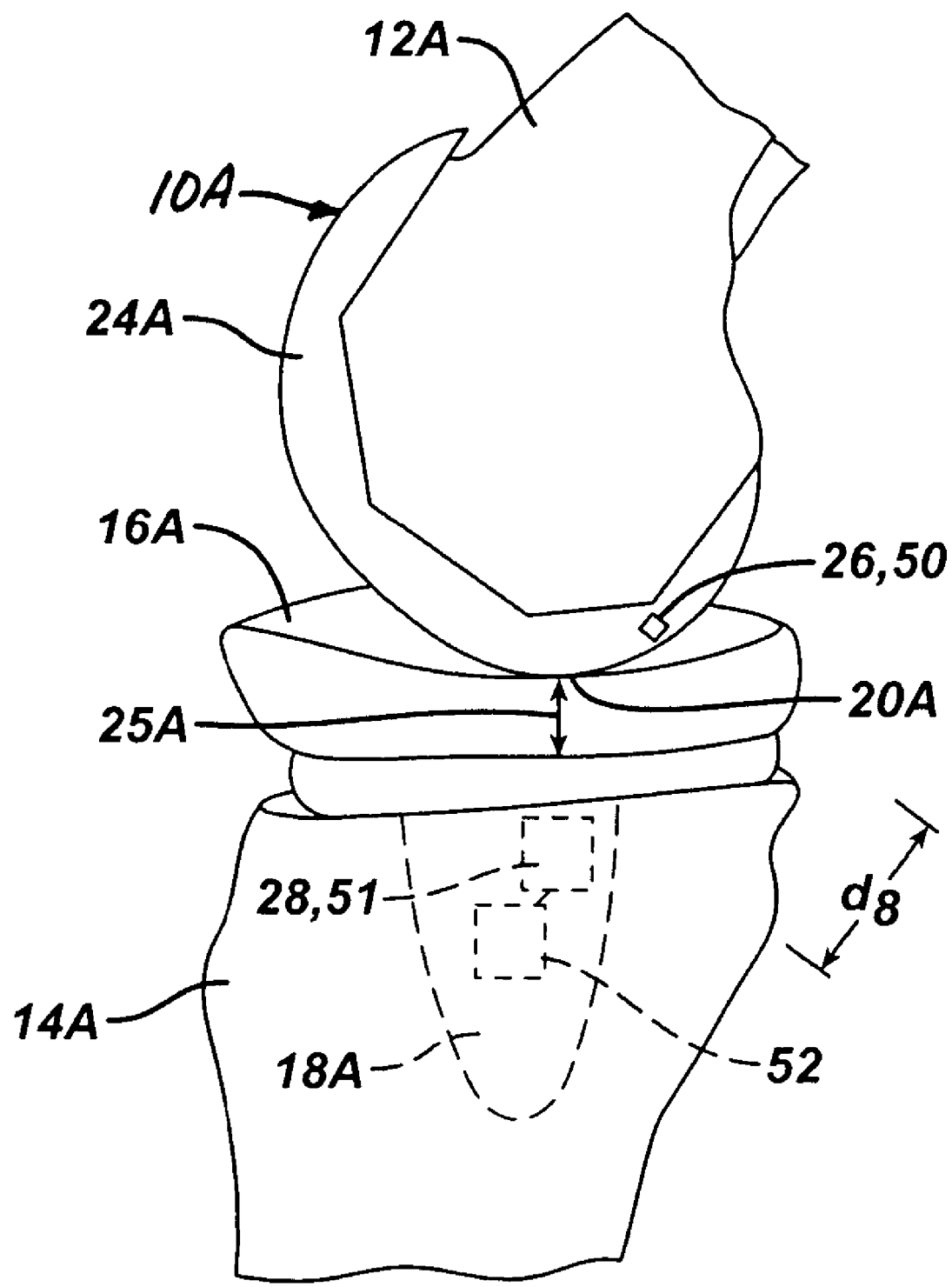
FIG. 8 is a side elevation of the knee joint endoprosthesis system of FIG. 7, showing the bones and prosthetic components when the leg is slightly flexed, as when the patient is walking.
Figure 9:
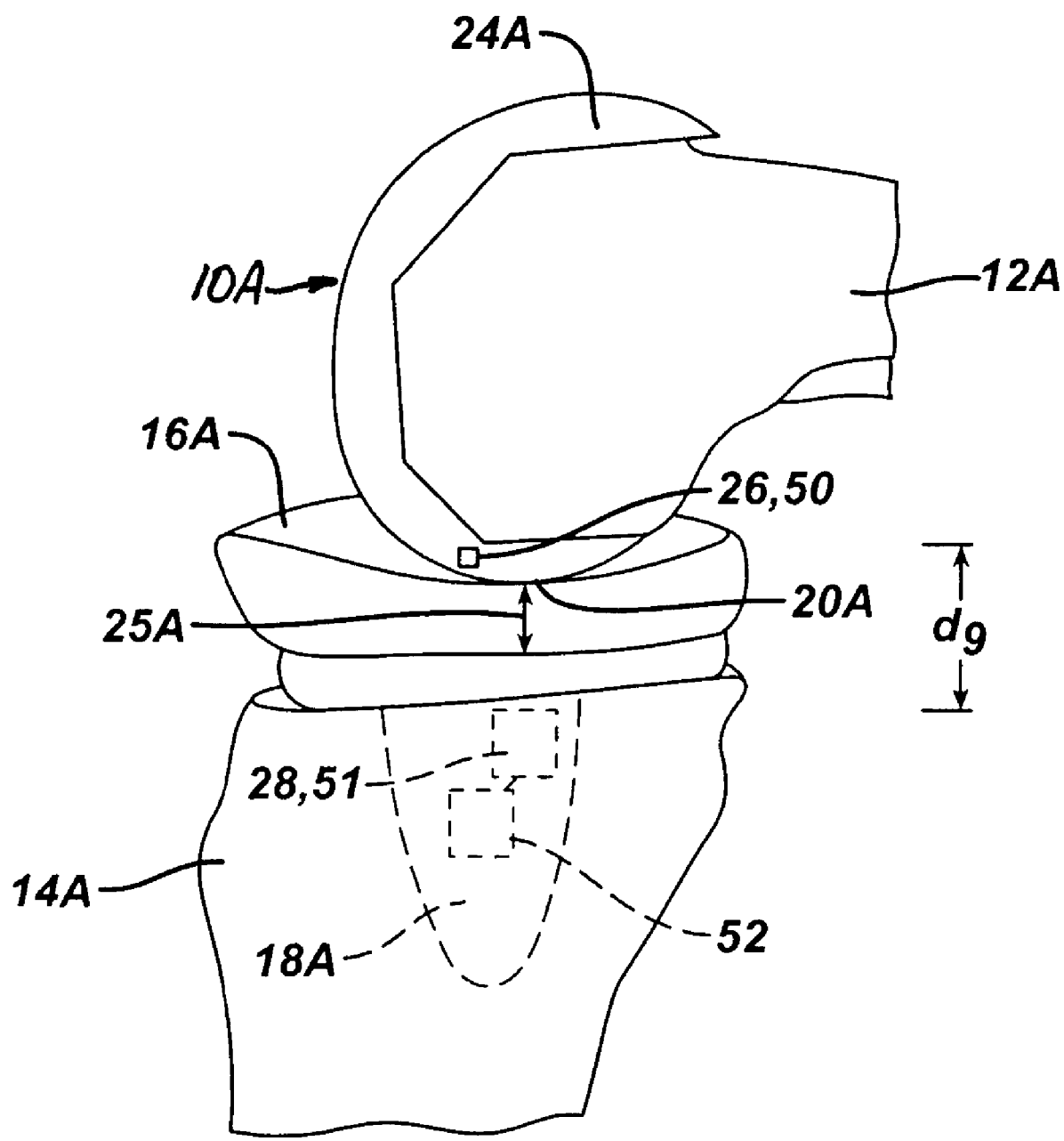
FIG. 9 is a side elevation of the knee joint endoprosthesis system of FIGS. 7–8, showing the bones and prosthetic components when the leg is fully flexed as when the patient is squatting.

Other types of proximity sensor systems could be used in the first illustrated embodiment. For example, in the embodiment of FIGS. 7–9, a radio-frequency (RF) transponder 50 is affixed on one side of the joint articulation 20A or joint space 25A. In FIGS. 7–9, the same reference numbers have been used for similar elements as those described above for the first illustrated embodiment, followed by the letter "A". In the knee system 10A of FIGS. 7–9, the RF transponder 50 (serving as a signal source 26) is affixed to the distal femoral component 24A. An RF receiver/demodulator 51 (serving as a sensor 28) is affixed to the proximal tibial component 18A on the opposite side of the joint articulation 20A or joint space 25A. Additional electronics 52 are affixed to the proximal tibial component 18A of the illustrated knee endoprosthesis system 10A. As shown schematically in FIG. 10, these additional electronics include a first power source 53, a digital logic element/pulse generator 54, a counter 56, a printed circuit board 58, an internal transmitter 60, a second power source 61, wiring 62 and solder (not shown).

The first power source 53 can be a battery as in the first illustrated embodiment. The second power source 61 can be a ferrite coil functioning like the second power source in the first illustrated embodiment, supplying power to the other electronics when an external power source 64 such as an electric coil is placed in proximity to the exterior of the knee joint in proximity to the ferrite coil power source 53. Alternatively, instead of providing a second power source 61, the power for the secondary system 60, 63 could come from the first power source 53 using an inductively activated switch.

The RF transponder 50 transmits an RF signal and the RF receiver/demodulator 51 receives the RF signal. The amplitude or phase of the signal received by the RF receiver/demodulator 51 varies with the distance between the RF transponder 50 serving as the signal source 26 and the RF receiver/demodulator 51 serving as the sensor 28. Thus, the specific distance between the RF transponder 50 and RF receiver/demodulator 51 is encoded in the transmittal signal; this distance is shown at "d" in FIG. 10. As shown in FIGS. 7–9, the RF transponder 50 and the RF receiver/demodulator 51 can be positioned on the implant components 18, 24 so that a specific distance between these components corresponds with a particular action, flexion or relative position of these implant components 18, 24. Thus, the RF transponder 50 and receiver/demodulator 51 can be positioned so that when the patient is standing as in FIG. 7, the distance $d_7$ between the RF proximity sensor components 50, 51 is at a maximum; when the patient's knee is flexed slightly as shown in FIG. 8, the distance $d_8$ between the RF proximity sensor components 50, 51 is an intermediate distance less than the maximum distance $d_7$; when the patient's knee is flexed to a position corresponding with sitting or squatting as shown in FIG. 9, the distance $d_9$ is at a minimum. Using the RF proximity sensor system 50, 51, each distance $d_7$, $d_8$ and $d_9$ is encoded in the transmittal signal and received by the RF receiver/demodulator 51.

Figure 10:
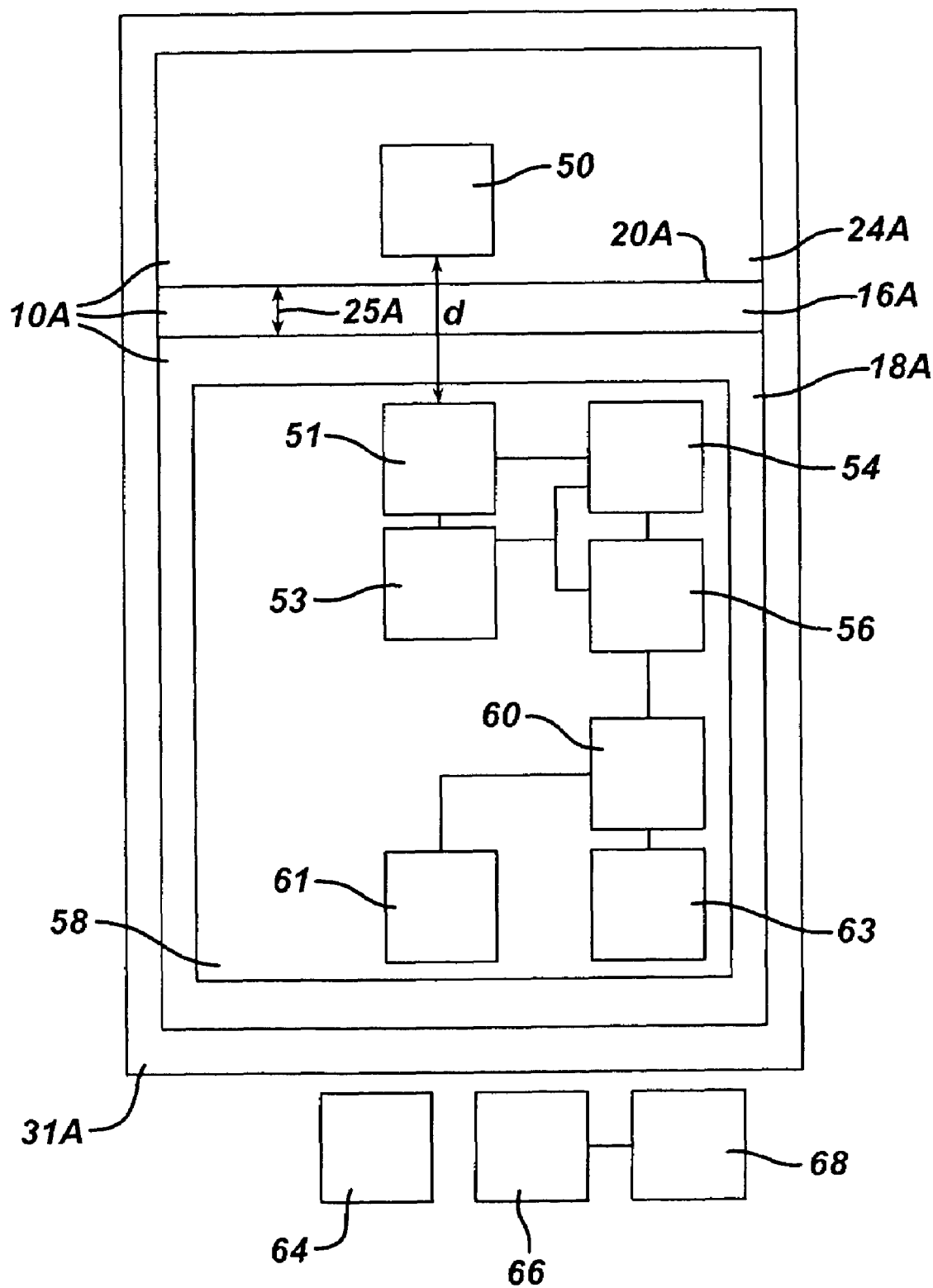
FIG. 10 is a schematic illustration of the components of the knee joint endoprosthesis system of FIGS. 7–9, showing external components as well as those implanted in the patient.
Figure 11:
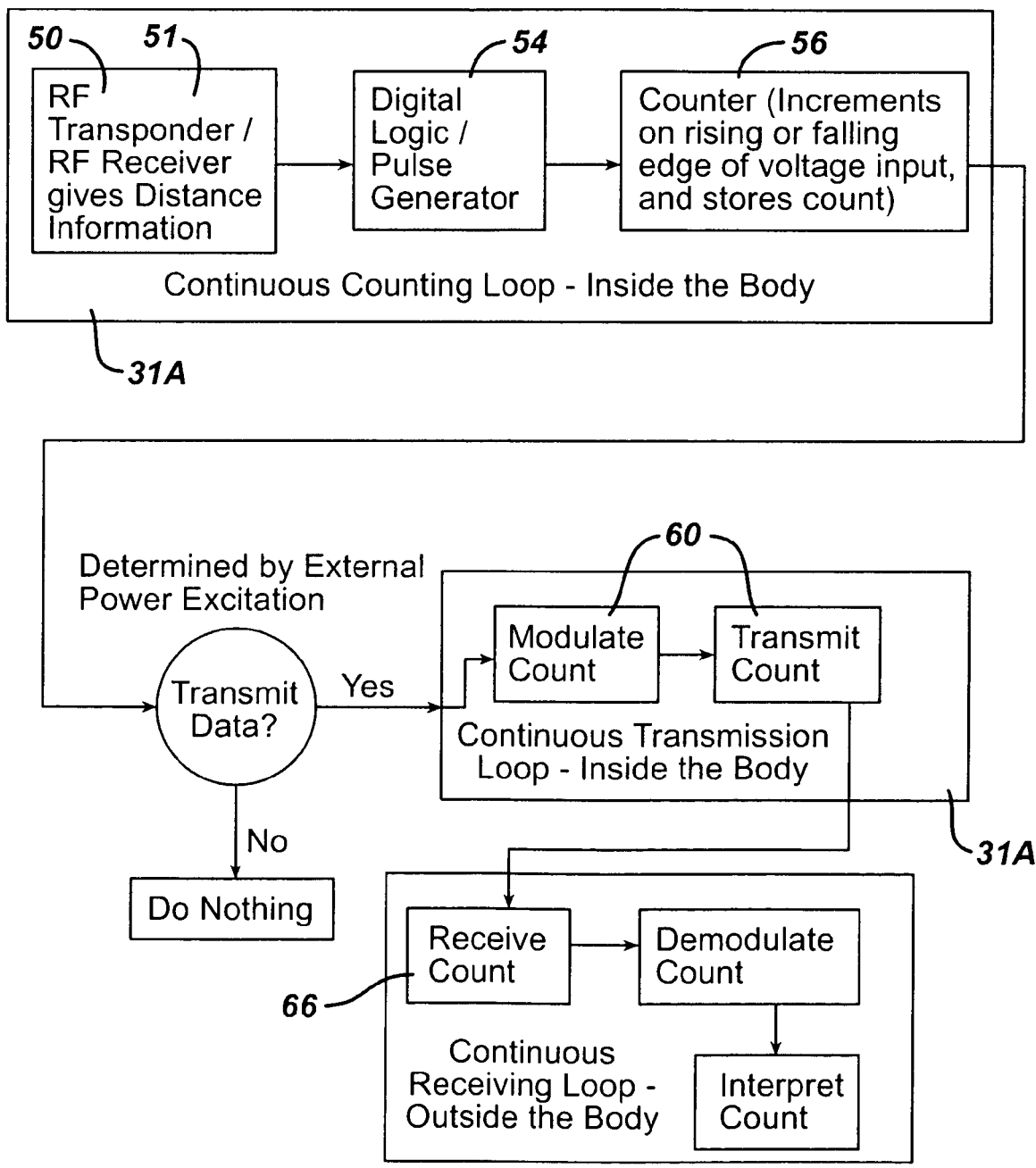
FIG. 11 is a flow chart illustrating use of the knee endoprosthesis system of FIGS. 7–10.

As shown in FIGS. 10–11, the RF receiver/demodulator 51 is electrically connected or coupled to the digital logic element/pulse generator 54 to deliver these signals to the digital logic element on a continuous basis. The digital logic element 54 also serves as a pulse generator, and generates an electric pulse each time an RF wave having a particular characteristic is received by the receiver/demodulator 51. The RF wave characteristic corresponding with any of the distances $d_7$, $d_8$ or $d_9$ can be selected as the characteristic that results in a pulse being created by the digital logic element 54. For example, the digital logic element can be set to generate a pulse each time an RF wave corresponding with the distance $d_8$ or $d_9$ is received by the RF receiver/demodulator 51. The digital logic element/pulse generator 54 is electrically connected or coupled to a counter 56 that records incremental pulses received from the digital logic element/pulse generator 54. Thus, a running count of the number of times the joint is in the position of FIG. 8 or FIG. 9 can be maintained by the counter 56. All of these steps take place within the patient's body shown at 31A in FIG. 11.

As indicated in the flow chart of FIG. 11, if the second internal power source 61 is not in proximity to an external power source 64, the incremental number of counts is stored within the prosthesis system 10A but is not transmitted outside of the patient's body 31A. Once an external power source 64 is brought into proximity with the second internal power source 61, power is supplied for operation of the modulator/transmitter 60 of the joint endoprosthesis system 10A.

When power is supplied to the modulator/transmitter 60, a signal is produced that is encoded with the incremental number received from the counter 56; in other words, the signal produced by the modulator/transmitter 60 has a unique characteristic corresponding with the incremental number of counts stored in the counter 56.

The modulator/transmitter 60 is connected or coupled to the internal antenna 63 so that the signal can be transmitted to an external receiver 66 located at the point of care. The external receiver 66 is connected or coupled to an external data interpretation device 68 such as a computer for interpretation of the encoded signal and conversion to a numerical count that can be read by the caregiver.

As in the first illustrated embodiment, the external receiver 66 can comprise a radio-frequency antenna that is connected to provide a signal to the data interpretation device 68. The data interpretation device 68 can be a standard computer programmed to convert the encoded signal received from the internal transmitter 60 and internal antenna. The data interpretation device 68 can also be programmed to perform calculations necessary to convert a particular signal into the number of cycles recorded by the counter 56. It is anticipated that a software engineer or programmer could readily program the external computer 68 to perform this calculation. This number of cycles can be compared to a base reference to determine if the patient's life style is likely to adversely affect the useful life on any one of the joint endoprosthesis components.

Thus, the joint endoprosthesis system of the present invention can utilize proximity sensors that generate a signature radio-frequency wave for a distance that corresponds with a particular angle α between the mechanical axes, a particular predetermined condition of the joint (e.g. bent as in FIG. 9), a particular degree of flexion, or a particular action of the patient (e.g., lifting the leg when walking as in FIG. 8). This wave signature can be converted to an incremental count that is stored or recorded and that can be selectively converted into another wave signature for transmission to external equipment for interpretation.

Other types of proximity sensors could be used in the joint endoprosthesis system of the present invention. For example, proximity sensors relying upon eddy currents could be used.

The illustrated knee endoprosthesis systems 10, 10A could be modified in several ways. For example, if there is greater concern with wear on the posterior side of the tibial bearing 16, 16A it may be desirable to set the positions and orientations of the signal source 26 and sensor 28 so that a signal is generated when the patient's joint is in the position shown in FIGS. 3 and 9 instead of when the patient's joint is in the position shown in FIGS. 2 and 8. Moreover, it may be desirable to provide a plurality of signal sources and sensors to maintain separate counts of the number of times the patient's joint is in the position shown in FIGS. 2 and 8 and the number of times the patient's joint is in the position shown in FIGS. 3 and 9.

Figure 12:
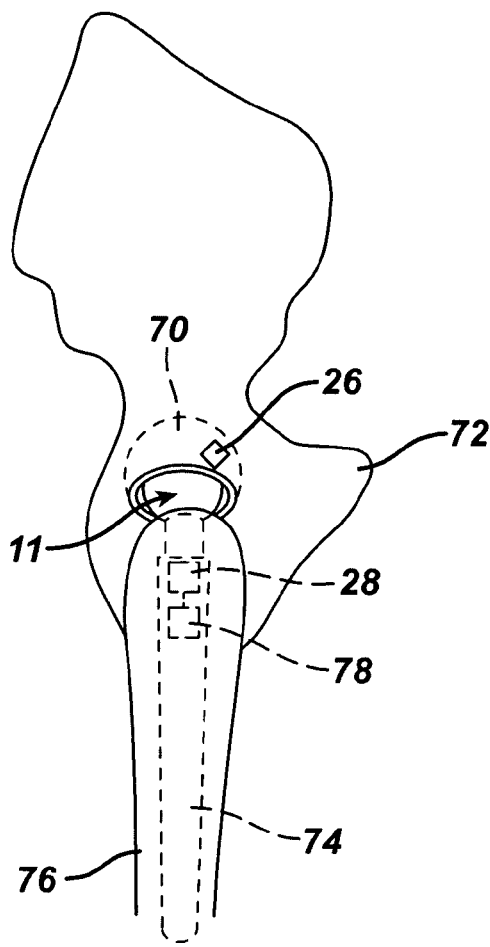
FIG. 12 is a side elevation of a hip joint endoprosthesis system implanted on a portion of the hipbone and proximal femur, showing the bones and prosthetic components in extension as when the patient is in a standing position.
Figure 13:
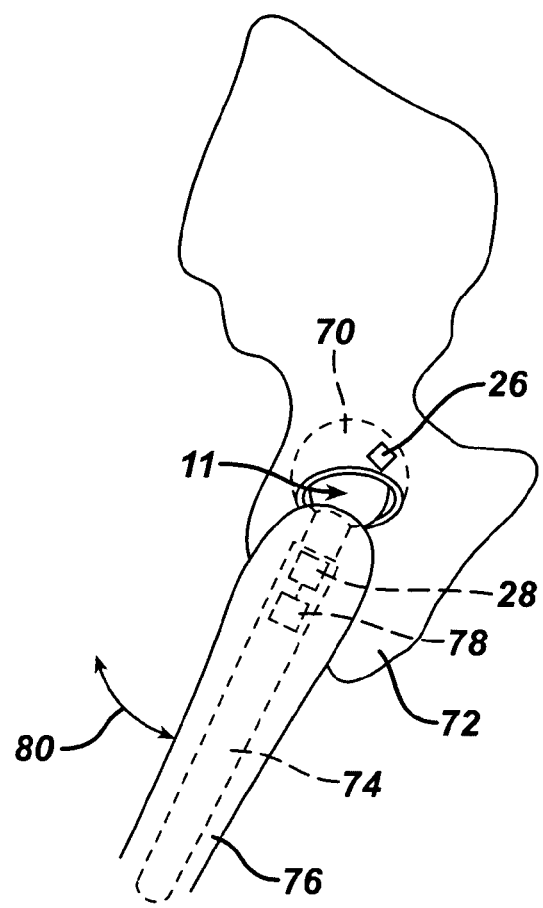
FIG. 13 is a side elevation of the hip joint endoprosthesis system of FIG. 12, showing the bones and prosthetic components when the hip is slightly flexed by rotation in a sagittal plane, as when the patient is walking.
Figure 14:
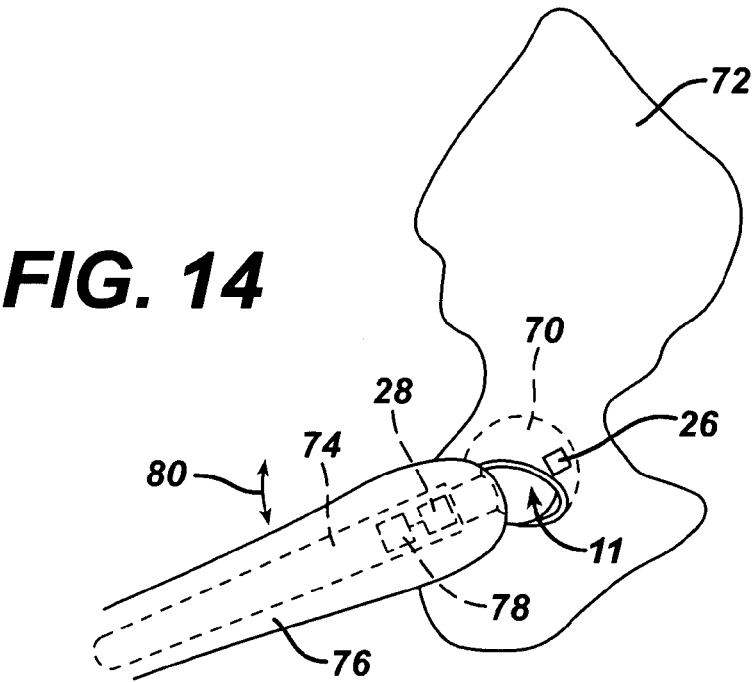
FIG. 14 is a side elevation of the hip joint endoprosthesis system of FIGS. 12–13, showing the bones and prosthetic components when the hip is fully flexed by rotation in a sagittal plane as when the patient is squatting.

Application of the principles of the present invention to hip endoprosthesis systems 11, 11A, 11B is illustrated in FIGS. 12–18. As shown in FIGS. 12–18, the first prosthetic component can comprise an acetabular shell 70, 70A, 70B affixed to the acetabulum of the hipbone or pelvis 72. The second prosthetic component can comprise a proximal femoral component 74, 74A, 74B affixed to the proximal femur 76. A sensor 28, 28A, 28B can be affixed to one of the prosthetic components and a signal source 26, 26A, 26B can be affixed to the other prosthetic component. In the illustrated embodiments, the sensor 28, 28A, 28B and other electronic components 78, 78A, 78B are affixed to the proximal femoral component 74, 74A, 74B and the signal source 26, 26A, 26B is affixed to the acetabular shell 70, 70A, 70B. The signal source 26 and sensor 28 can be positioned and aligned so that the system counts hip flexion in the sagittal plane, as shown in FIGS. 12–14, with the counter recording the number of times the prosthetic components 70, 74 are in one of the positions shown in FIGS. 12–14 to record movement in the directions indicated by arrow 80.

Figure 15:
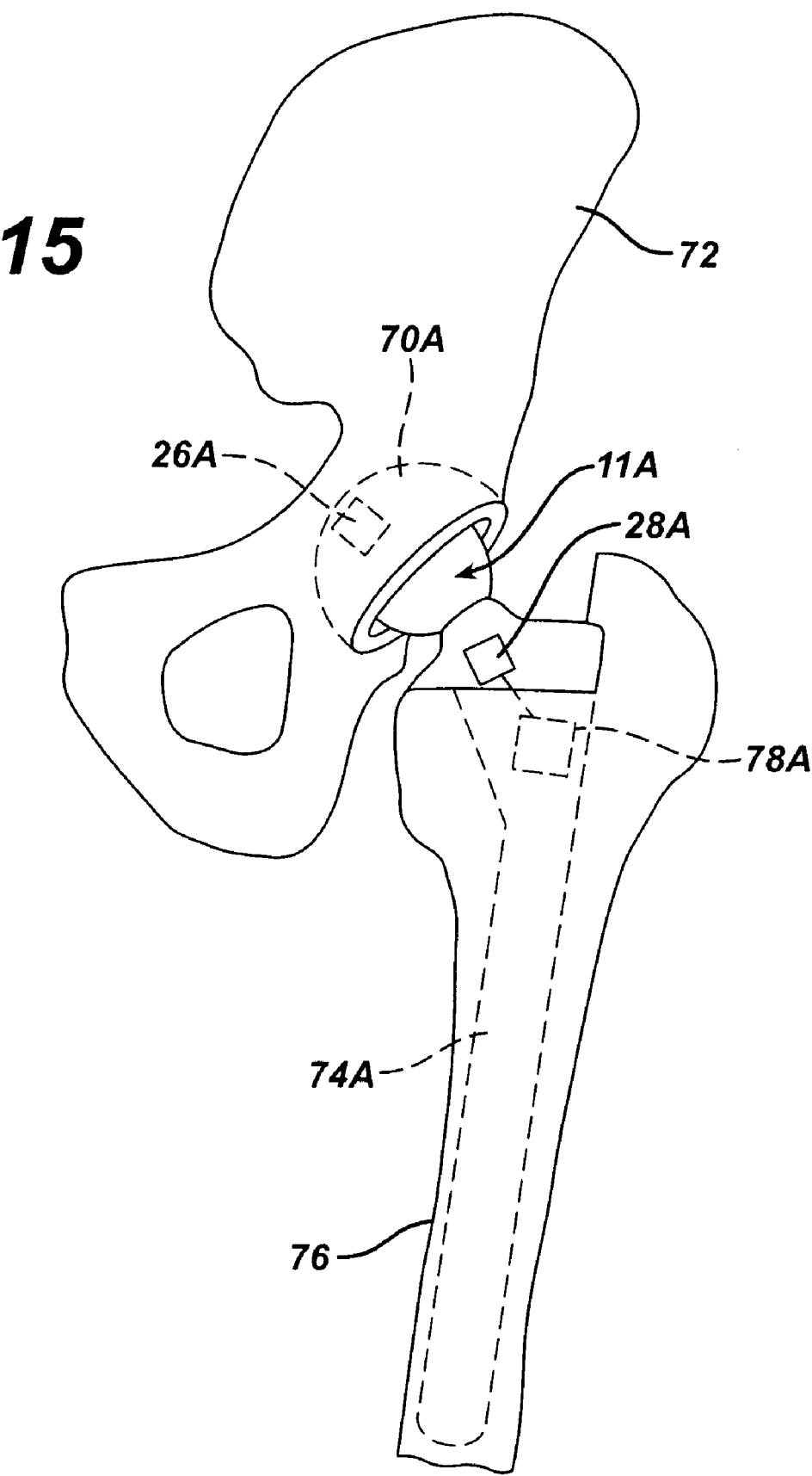
FIG. 15 is a front elevation of a hip joint endoprosthesis system implanted on a portion of the hipbone and proximal femur, showing the bones and prosthetic components in extension as when the patient is in a normal standing position.
Figure 16:
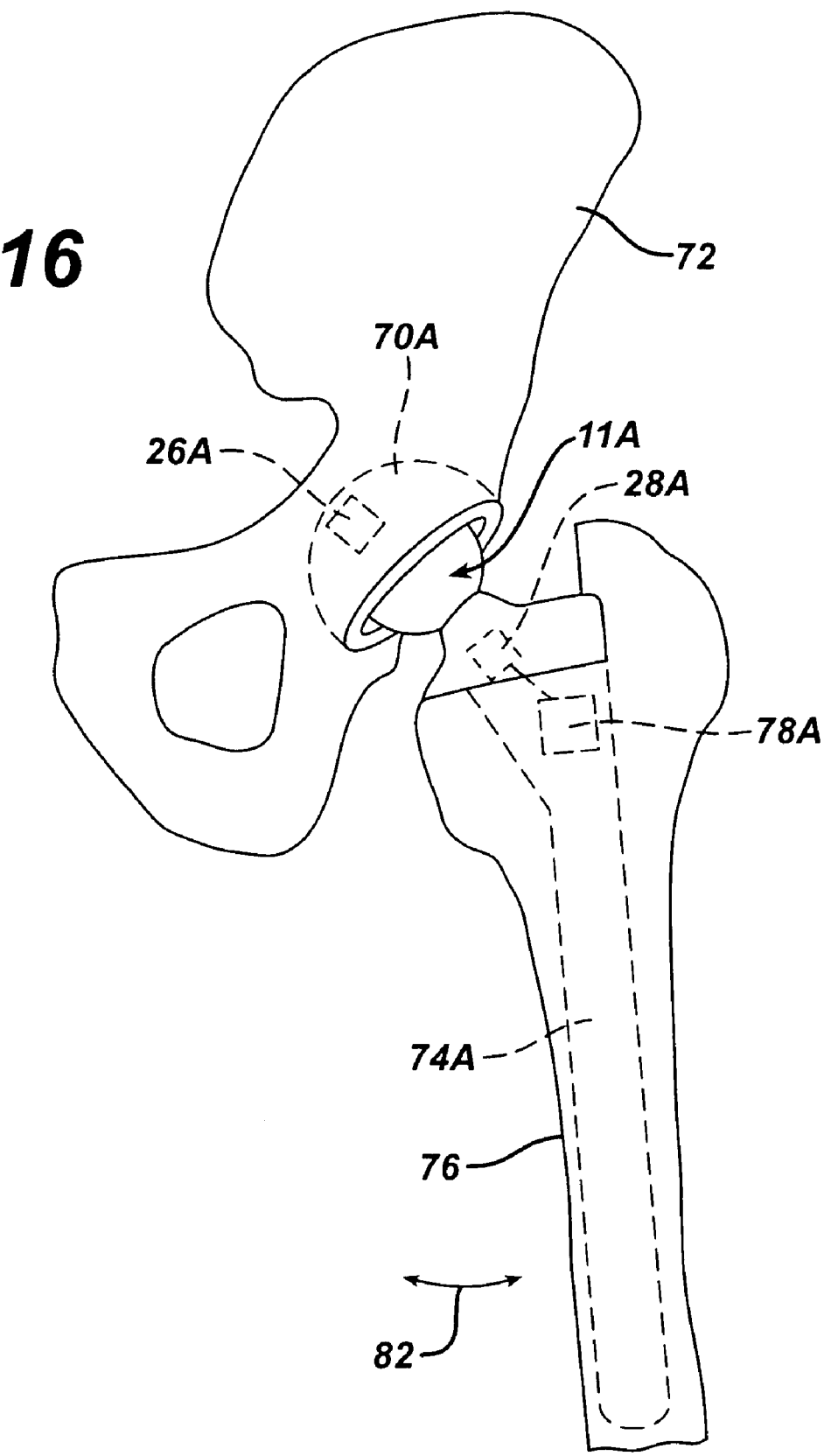
FIG. 16 is a front elevation of the hip joint endoprosthesis system of FIG. 15, showing the bones and prosthetic components when the hip is slightly abducted by rotation in a coronal plane.
Figure 17:
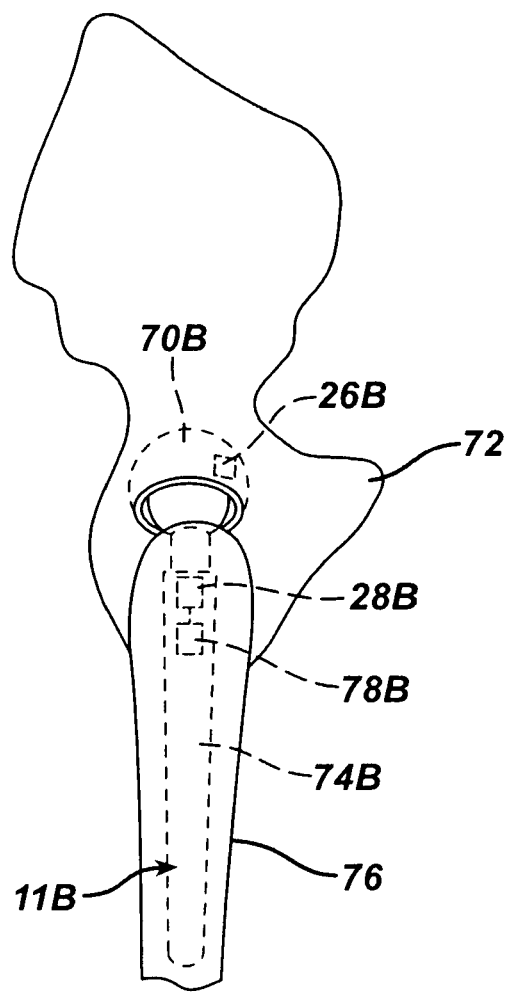
FIG. 17 is a side elevation of a hip joint endoprosthesis system implanted on a portion of the hipbone and the proximal femur, showing the bones and prosthetic components in extension as when the patient is in a normal standing position.
Figure 18:
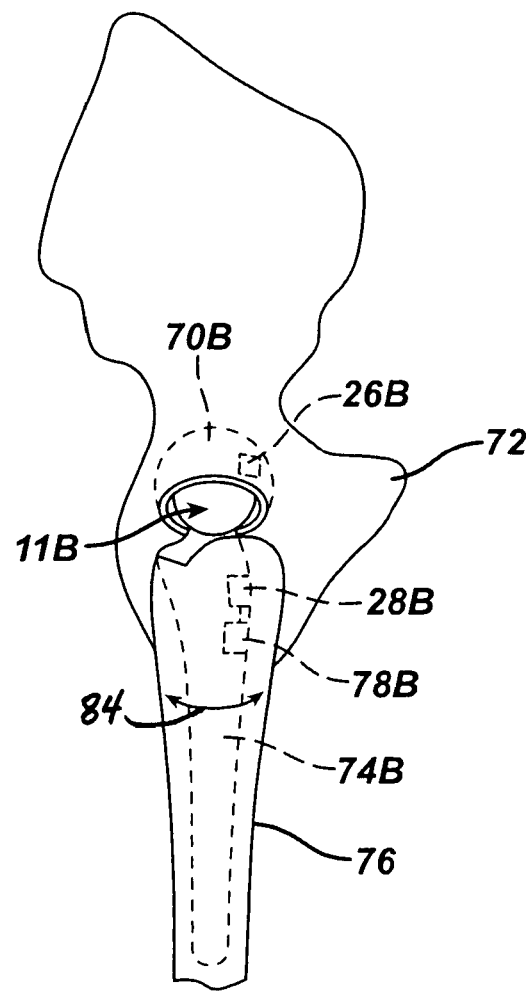
FIG. 18 is a side elevation of the hip joint endoprosthesis system of FIG. 17, showing the bones and prosthetic components when the femur and femoral prosthetic component are rotated slightly in a transverse plane.

As shown in FIGS. 15–16, the signal source 26A and sensor 28A can also be positioned and oriented to record the number of times the prosthetic components 70A, 74A undergo adduction or abduction, recording movement in a coronal plane. This direction of movement is indicated by arrow 82. In addition, the signal source 26B and sensor 28B can be positioned and oriented to record the number of times the femoral component 74B is rotated about a longitudinal axis of the femur in the direction indicated by arrow 84 in FIG. 18. A hip endoprosthesis system could include proximity sensors that record any of these movements, some of these movements, or all of these movements.

The elements serving as the signal source 26, 26A, 26B and sensor 28, 28A, 28B can be any of those described above for the knee endoprosthesis systems 10, 10A. In addition, the electronics 78, 78A, 78B associated with the signal source 26, 26A, 26B and sensor 28, 28A, 28B can be like those described above for the knee endoprosthesis systems 10, 10A. Use of the illustrated hip endoprosthesis systems 11, 11A, 11B would be similar to that described above for the knee endoprosthesis systems.

Application of the principles of the present invention to a shoulder endoprosthesis system 13 is illustrated in FIGS. 19–21. As shown in FIGS. 19–21, the first prosthetic component can comprise a humeral component 92 and the second prosthetic component can comprise a glenoid component 94. A sensor 28 can be affixed to one of the prosthetic components 92 or 94 and a signal source 26 can be affixed to the other prosthetic component 92 of 94. In the illustrated embodiment, the sensor 28 and other electronic components 96 are affixed to the proximal humeral component 92 and the signal source 26 is affixed to the glenoid component 94. The signal source 26 and sensor 28 can be positioned and aligned so that the system counts shoulder flexion in the coronal plane, as shown in FIGS. 19–21, with the counter recording the number of times the prosthetic components 92, 94 are in one of the positions shown in FIGS. 19–21 to record movement in the directions indicated by arrow 98. The signal source 26 and sensor 28 can also be positioned and oriented to record the number of times the prosthetic components 92, 94 undergo movement in a sagittal or transverse plane. A shoulder endoprosthesis system 13 could include proximity sensors that record any of these movements, some of these movements, or all of these movements.

The elements serving as the signal source 26 and sensor 28 for the shoulder endoprosthesis system 13 can be any of those described above for the knee and hip endoprosthesis systems 10, 10A, 11, 11A, 11B. In addition, the electronics 96 associated with the signal source 26 and sensor 28 for the shoulder endoprosthesis system 13 can be like those described above for the knee and hip endoprosthesis systems 10, 10A, 11, 11A, 11B.

Use of the illustrated shoulder endoprosthesis system 13 would be similar to that described above for the knee and hip endoprosthesis systems 10, 10A, 11, 11A, 11B. These principles of the present invention could be applied to other joint endoprostheses as well, such as in the elbow, wrist, ankle or other extremities.

In all of the illustrated embodiments, the signal source, sensor and associated electronics could be held in recesses in the associated endoprosthesis components. FIGS. 22–23. illustrate recesses 100, 101 in the body 102, 103 of endoprosthesis components. The body 102, 103 can be any of the components described above, such as the proximal tibial component 18, 18A, the tibial bearing 16, 16A, the distal femoral component 24, 24A, the proximal femoral component 74, 74A, 74B, the acetabular cup or shell 70. 70A, 70B, the acetabular liner, the humeral component 92, the glenoid component 94, or analogous components of other prosthetics. The recesses 100, 101 would be formed in areas of the endoprosthesis components where the presence of the recesses does not adversely affect the mechanical or physical properties of the endoprosthesis components. In the illustrated embodiments, the recesses or cavities 100, 101 extend inward from a non-articulating surface of the body 102, 103 of the endoprosthesis component.

The sizes of the components 26, 28, 30, 30A, 50, 51, 78, 96 can be selected to minimize the amount of space required to be taken up by these components. Components can be combined if desired. The signal source 26, 50 sensor 28, 51 and associated electronics 30, 30A, 78, 96 can be permanently affixed in these recesses with a suitable adhesive if desired. The illustrated systems are assembled prior to implantation of the endoprosthesis system. The recesses or cavities 100, 101 can be sealed by any appropriate means after the components 26, 26A, 26B, 50, 30, 52, 78, 78A, 78B, 96, 30A, 30B, 30C are in place. For example, the openings to the recesses or cavities 100, 101 could be welded closed or a sealant such as a biocompatible epoxy or polyurethane, could be poured over the recess or cavity as a liquid and allowed to cure to thereby permanently secure the components in the body of the prosthetic component. Cured sealant is indicated at 104 and 105 in FIGS. 22–23. The illustrated systems are assembled prior to implantation of the illustrated endoprosthesis systems.

It should be understood that while the signal source 26 is shown in solid rather than phantom lines in some of the accompanying drawings, this element would generally all be within the interior of the prosthetic component or on or within bone rather than on an exposed surface of a prosthetic component, although it may be possible or desirable to mount some of the electronics on a surface of one of the implants. Moreover, some of these electronic components could alternatively be formed as integral parts of the associated endoprosthesis components 18, 18A, 24, 24A, 70, 70A, 70B, 74, 74A, 74B, 92, 94.

In all of the illustrated embodiments, it is anticipated that suppliers of the signal source, sensor and associated electronics can provide design assistance to minimize the size of these components.

Other variations in the illustrated embodiments are possible. For example, the endoprosthesis system can be provided in the form of a kit with one or more of the electronic and signal generating components provided as a discrete element. For example, the electronic components 30, 30A, 51, 78, 96 and sensor 28, 28A, 28B, 51 could be supplied as one or more separate discrete packages to be affixed to the patient's bones instead of to the components of the implant itself. Alternatively, the signal source 26, 26A, 26B, 50 could be supplied as a separate discrete component to be affixed to the patient's bone. Moreover, all of the electronic components 30, 30A, 30B, 52, 78, sensor 28, and the signal source 26, 26A, 26B, 50 could be supplied as separate discrete components to be affixed to the patient's bones.

Other types of measurements can be made and incrementally counted as well. For example, based on the fact that each knee or hip joint periodically bears the load of the patient's weight during walking or running, the joint endoprosthesis system could include a load cell or strain gauge as the sensor as shown at 28C in FIGS. 24–25. In such a case, the "signal source" would comprise the load that occurs as a result of joint motion. For a knee endoprosthesis system as in FIG. 24, the load cell or strain gauge serving as the sensor 28C could be affixed in the prosthetic tibial component 18C or in the tibial bearing 16C and electrically connected or coupled to internal electronics 30C including a counter so that the counter incrementally records each time the load on the prosthetic tibial component or tibial bearing exceeds a predetermined value. For a hip endoprosthesis system as in FIG. 25, the load cell or strain gauge serving as the sensor 28C could be affixed in the proximal femoral component 74C or in the acetabular liner 70C and electrically coupled to internal electronics 78C so that the counter incrementally records each time the load on the proximal femoral component or acetabular liner exceeds a predetermined value. Such measurements could be taken in addition to cycle counters relying on proximity sensors or as alternatives to the use of proximity sensors. The incremental counts created by such systems can be transmitted to external receivers outside the patient's body in the manners described above for the other illustrated embodiments. These components 28C, 30C, 78C can be mounted to the prosthetic components as shown in FIGS. 22–23. A similar system could be used with a shoulder endoprosthesis system or other prosthetic system where a load or strain is experienced by one or more of the prosthetic components. The counts of excessive loads on the prosthetic components of the joint endoprosthesis systems can be also used to counsel patient's regarding life-style changes if the counts exceed that which is considered standard for patients.

The joint endoprostheses of the present invention could be combined with other electronic features. For example, an electronic component with recorded information regarding the prosthetic implant could be included, or this information could be recorded on one of the electronic components described above. The joint endoprosthesis systems of the present invention can also be combined with joint space measurement devices such as those described in U.S. Provisional Patent Application Ser. No. 60/486,615, entitled "In Vivo Joint Space Measurement Device and Method," filed on Jul. 11, 2003 by Mark R. DiSilvestro, and the corresponding U.S. regular utility patent application Ser. No. filed on Jul. 9, 2004 by Mark R. DiSilvestro, Terry L. Dietz and Jason T. Sherman, the complete disclosures of which are incorporated by reference herein.

And while the present invention has been described with respect to post-implantation patient care, the principles of the present invention could be applied to other uses as well, such as in intraoperative assessment of the prosthetic implant.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A joint endoprosthesis system to be implanted in a patient, the system comprising:
   a first prosthetic component having a bone engaging surface to be affixed to one bone of the joint and an articulation surface;
   a second prosthetic component having a bone-engaging surface to be affixed to the other bone of the joint and a second surface spaced from the bone-engaging surface;
   the first and second prosthetic components being capable of relative articulation;
   an electromagnetic field source affixed directly to one of the prosthetic components, the electromagnetic field source having a pole in a fixed position and orientation with respect to the prosthetic component to which it is affixed and a maximum magnetic field strength in a fixed orientation with respect to the prosthetic component to which it is affixed;
   a sensor having characteristics allowing it to generate a signal each time the magnetic field strength at the sensor exceeds a predetermined threshold and to refrain from generating a signal when the magnetic field strength at the sensor falls below the predetermined threshold, the sensor being affixed directly to the other prosthetic component and being in a fixed position with respect to the bone-engaging surface of the prosthetic component to which it is directly affixed; and
   a counter electrically connected to the sensor for storing the number of signals generated by the sensor, the counter being affixed directly to one of the first and second prosthetic components for implantation with the prosthetic component;
   wherein the electromagnetic field source and sensor are positioned and oriented so that the electromagnetic field strength at the sensor is above the threshold of the sensor when the first and second prosthetic components are articulated in one orientation and so that the electromagnetic field strength falls below the threshold of the sensor when the first and second prosthetic components are articulated in a plurality of orientations.

2. The joint endoprosthesis system of claim 1 wherein the sensor comprises a transducer.

3. The joint endoprosthesis system of claim 1 further comprising a first power source for supplying continuous power to the counter.

4. The joint endoprosthesis system of claim 1 further comprising a transmitter for transmitting data related to the number of signals stored.

5. The joint endoprosthesis system of claim 4 further comprising:
   a first power source for supplying continuous power to the counter; and
   a second power source for selectively supplying power to the transmitter.

6. A joint endoprosthesis system comprising:
   a first prosthetic component to be affixed to one bone of the joint, the first prosthetic component having a non-articulating surface and a recess in the non-articulating surface;
   a second prosthetic component to be affixed to the other bone of the joint, the second prosthetic component having a non-articulating surface and a recess in the non-articulating surface;
   a bearing to be carried by one of the prosthetic components and positioned between the first and second prosthetic components;
   an electromagnetic field source;
   a sensor for generating a signal each time the bones are in a predetermined position, the sensor being permanently affixed directly to one of the prosthetic components;
   a counter electrically connected to the sensor for storing the incremental number of signals generated by the sensor, the counter being permanently affixed directly to one of the first and second prosthetic components;
   a transmitter electrically connected to the counter for selectively transmitting a signal having a characteristic related to the incremental count recorded by the counter, the transmitter being permanently affixed directly to one of the first and second prosthetic components;
   a first power source electrically connected to the counter for supplying continuous power to the counter; and
   a second power source electrically connected to the transmitter for selectively supplying power to the transmitter;
   wherein the electromagnetic field source is received and sealed in the recess of one of the prosthetic components and the sensor, counter and first power source are received and sealed in the recess of the other prosthetic component.

7. The joint endoprosthesis system of claim 6 wherein the sensor comprises a switch.

8. The joint endoprosthesis of claim 7 wherein the sensor comprises a Hall effect switch and the electromagnetic field source comprises a permanent magnet.

9. The joint endoprosthesis of claim 6 wherein the first prosthetic component comprises a distal femoral component and the second prosthetic component comprises a proximal tibial component.

10. The joint endoprosthesis system of claim 6 wherein the first power source and the second power source are affixed to the second prosthetic component.

11. A method of monitoring use of a joint endoprosthesis system implanted within the body of a patient, wherein the joint endoprosthesis system includes a first prosthetic component affixed to one bone of the joint of the patient and a second prosthetic component affixed to another bone of the joint of the patient, wherein at least one of the prosthetic components includes a sensor, a counter and a transmitter and wherein the other prosthetic component includes an electromagnetic field source, and wherein the first and second prosthetic components are movable through a plurality of positions, the method comprising the steps of:

generating a signal each time the first and second prosthetic components are in a predetermined position;

storing an incremental count of the number of signals generated, wherein the count is stored in the counter within the patient's body;

converting the incremental count stored into a transmittable signal, wherein the count is converted within the patient's body;

transmitting the transmittable signal to a Position outside of the patient's body; and determining the incremental count outside of the patient's body.

* * * * *